United States Patent
McConnell et al.

(10) Patent No.: US 9,555,963 B2
(45) Date of Patent: *Jan. 31, 2017

(54) SYSTEM AND APPARATUS FOR WASTE DISPOSAL AND CHANGING INFANT-TODDLER BEHAVIOR

(71) Applicant: Thomas E. McConnell, Santa Maria, CA (US)

(72) Inventors: Thomas E. McConnell, Santa Maria, CA (US); Yafei Lu, Jiangsu (CN)

(73) Assignee: Thomas E. McConnell, Santa Maria, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/838,267

(22) Filed: Aug. 27, 2015

(65) Prior Publication Data

US 2016/0060028 A1 Mar. 3, 2016

Related U.S. Application Data

(63) Continuation-in-part of application No. 14/838,247, filed on Aug. 27, 2015, which is a continuation-in-part of application No. 14/473,766, filed on Aug. 29, 2014, which is a continuation-in-part of application No. 14/473,685, filed on Aug. 29, 2014.

(51) Int. Cl.

| | |
|---|---|
| *G09B 19/00* | (2006.01) |
| *B65F 1/06* | (2006.01) |
| *G09B 5/00* | (2006.01) |
| *G01N 21/84* | (2006.01) |
| *B65F 1/14* | (2006.01) |
| *B65F 1/00* | (2006.01) |
| *B65F 1/16* | (2006.01) |

(52) U.S. Cl.
CPC .............. *B65F 1/06* (2013.01); *B65F 1/1607* (2013.01); *G01N 21/84* (2013.01); *G09B 5/00* (2013.01); *G09B 19/00* (2013.01); *B65F 1/0006* (2013.01); *B65F 1/1623* (2013.01); *B65F 2001/1676* (2013.01); *B65F 2210/1675* (2013.01); *B65F 2220/128* (2013.01); *B65F 2240/132* (2013.01)

(58) Field of Classification Search
USPC ........ 434/236, 247; 446/236, 241, 243, 246, 446/256, 257; 53/469, 567; 220/495.01, 220/495.06, 495.08
See application file for complete search history.

(56) References Cited

U.S. PATENT DOCUMENTS

| | | | | |
|---|---|---|---|---|
| 3,321,103 | A | 5/1967 | Phillips | |
| 4,618,330 | A * | 10/1986 | Abe | A63H 1/06 446/236 |
| 4,643,692 | A * | 2/1987 | Magers | A63H 1/20 446/236 |
| 5,125,526 | A * | 6/1992 | Sumanis | B65F 1/06 220/263 |
| 5,238,440 | A * | 8/1993 | Morin | A63H 1/06 273/142 E |
| 5,314,338 | A * | 5/1994 | Caveza | G09B 19/00 434/259 |
| 5,799,909 | A * | 9/1998 | Ziegler | B65F 1/1415 220/481 |
| 6,719,194 | B2 * | 4/2004 | Richards | B65F 1/062 220/263 |
| 6,851,251 | B2 * | 2/2005 | Stravitz | B09B 3/0025 53/370 |

(Continued)

*Primary Examiner* — Kurt Fernstrom
(74) *Attorney, Agent, or Firm* — WPAT, P.C.; Anthony King

(57) ABSTRACT

A diaper pail having a top chamber with top transparent doors, and a transparent outer casing, allowing a user to see the rotating inner barrel as it spins within the transparent outer casing. The inner barrel holds a disposable bag and as it rotates the inner barrel untwists the neck of the bag, thus opening the bag for a soiled diaper to fall into the bag from the top chamber, and then the bag returns to its original twisted closed configuration. The soiled diaper falls into the bag while the doors of the top chamber remain shut, keeping malodorous gas from escaping. The visual spectacles provided by this diaper pail also act to change infant and toddler behavior by associating diaper change with a fun and fascinating event.

16 Claims, 35 Drawing Sheets

(56) References Cited

U.S. PATENT DOCUMENTS

| | | | | |
|---|---|---|---|---|
| 7,503,152 B2* | 3/2009 | Stravitz | .................... | B65B 9/15 53/211 |
| 7,594,376 B2* | 9/2009 | Chomik | .................... | B65B 7/12 53/370 |
| 7,660,724 B2* | 2/2010 | Mallett | .............. | A61B 19/0248 206/366 |
| 7,696,711 B2* | 4/2010 | Pollack | .................... | B65F 1/06 318/466 |
| 7,712,285 B2* | 5/2010 | Stravitz | .................... | B65F 1/12 200/61.62 |
| 7,958,704 B2* | 6/2011 | Stravitz | .................... | B65B 9/15 206/303 |
| 8,127,519 B2* | 3/2012 | Stravitz | ................ | B65F 1/0006 53/469 |
| 8,266,870 B1 | 9/2012 | Stravitz | | |
| 8,567,157 B2* | 10/2013 | Dunn | .................... | B65F 1/0006 220/495.06 |
| 8,833,592 B2* | 9/2014 | Dunn | .................... | B65F 1/0006 220/495.06 |
| 8,844,751 B2* | 9/2014 | Sakaguchi | ................ | B65F 1/06 220/253 |
| 2002/0038535 A1* | 4/2002 | Jensen | .................... | B65B 9/15 53/459 |
| 2006/0237461 A1* | 10/2006 | Chomik | .................... | B65B 7/12 220/495.06 |
| 2008/0019618 A1 | 1/2008 | Dayton et al. | | |

* cited by examiner

SYSTEM AND APPARATUS FOR WASTE DISPOSAL AND CHANGING INFANT-TODDLER BEHAVIOR

CROSS-REFERENCE TO RELATED APPLICATIONS

This application claims priority to, and is a Continuation-In-Part of, U.S. patent application Ser. No. 14/838,247, filed on Aug. 27, 2015, which is a Continuation-In-Part of U.S. patent application Ser. No. 14/473,776, filed on Aug. 29, 2014, which is a Continuation-In-Part of U.S. patent application Ser. No. 14/473,685, filed on Aug. 29, 2014, all of which are hereby incorporated by reference in their entireties. Although incorporated by reference in its entirety, no arguments or disclaimers made in the parent applications apply to this Continuation-In-Part application. Any disclaimer that may have occurred during the prosecution of the above-referenced applications is hereby expressly rescinded. Consequently, the Patent Office is asked to review the new set of claims in view of all of the prior art of record and any search that the Office deems appropriate.

BACKGROUND OF THE DISCLOSURE (1). Field of the Disclosure

The field of the disclosure relates to disposal systems of malodorous waste packages, namely soiled diapers.

(2). Description of Related Art Including Information Disclosed Under 37 CFR 1.97 and 1.98

Soiled diapers and/or other waste items can generate unpleasant odors, especially over extended time periods. Consequently, placing such waste items in a waste container that does not provide adequate sealing can result in the undesirable result of having odors escape into the surrounding environment.

At present, there are numerous diaper disposal pails on the market; however, none are entirely satisfactory. Diaper pails presently on the market simply have tops that cover a container housing the soiled diapers, yet such tops are not hands-free; They therefore require a user to grasp a handle, a latch, or the like to open the container in order to dispose of the diaper. Accordingly, such diaper pails serve as adequate disposal containers, yet are still unable to contain or mask the stench of soiled diapers because upon opening the diaper pail top, the stench will almost certainly waft out of the container. Some diaper pails have add-on products such as carbon filters or baking soda cartridges to absorb or neutralize odors; these may not be completely effective solutions given that the bags within the diaper pails are not sealed off to prevent odors from escaping once the top of the diaper pail is opened.

Other diaper pails such as U.S. Pat. No. 8,127,519, which is incorporated herein by reference in its entirety, have flexible material separating the main body cavity of the pail from an upper portion of the pail. However, such diaper pails still do not afford hands-free disposal and require the user to forcefully push the diaper by hand through the flexible webbing into the main body cavity of the pail. In addition, although there may be a twisting mechanism in an effort to contort and seal off a neck of the bag, the flexibility of the material fails to create a tight seal thereby leaving gaps allowing odors to escape through the bag opening.

Another receptacle such as that illustrated in U.S. Pat. No. 5,125,526, which is incorporated herein by reference in its entirety, discloses a receptacle with a rotatably mounted holder. When a user steps on a foot pedal, the holder rotates to twist and untwist a bag. While an upper portion of the bag is fixed to the receptacle, a lower portion of the bag is adhered to the holder using a double-sided adhesive tape so that the bag rotates with the holder. However, this receptacle has its disadvantages in that the bag maintains its twisted formation only when the top is closed. Upon pressing down the foot pedal, the top opens, the holder rotates, and the bag opens causing the unpleasant odors to flow out of the open bag.

Accordingly, there is a continuing need for an improved diaper pail or waste container having a hands-free or touch-free means for enhanced confinement of malodorous waste objects deposited into a container thereby retaining and preventing offensive odors from being emitted from the waste container. In other words, a desired waste disposal system would feature a means of depositing waste into a container while maintaining the bag in a closed formation for at least the duration of time that the top is open so that the user would not have to risk inhaling undesirable odors.

All referenced patents, applications and literatures are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply. The disclosure may seek to satisfy one or more of the above-mentioned desires. Although the present disclosure may obviate one or more of the above-mentioned desires, it should be understood that some aspects of the disclosure might not necessarily obviate them.

BRIEF SUMMARY OF THE DISCLOSURE

Improved embodiments of a diaper pail or a waste disposal system which can also serve to provide positive reinforcement of infant-toddler behavior in child development are hereby disclosed. The general concept is to provide a diaper pail or waste receptacle that comprises a feature such that a user may dispose of malodorous waste without the risk of inhaling unpleasant odors.

In some embodiments the waste disposal system features a top chamber that acts as a staging area before the soiled diaper is dropped into the disposable bag below the top chamber. The top chamber can have at least one door and when a soiled diaper is dropped or tossed through the door of the top chamber, the soiled diaper can temporarily stay in the top chamber while the door is closed. After the door is closed, the user can selectively open the disposable bag below the top chamber for the soiled diaper to drop into the disposable bag's main cavity. The user can then selectively close the bag. In one embodiment, the door of the top chamber opens and closes independently of the opening and closing of the disposable bag.

In further contemplated embodiments, this waste disposal system can have at least one attachment mechanism within an inner barrel of the waste receptacle. The attachment mechanism can be a hook, a peg, or a clip to engage with the disposable bag. The disposable bag can have a corresponding structure to detachably couple with the attachment mechanism. In some embodiments, the corresponding structure of the disposable bag is at least a hole, a sleeve, a strip, a loop, or a reinforced tab.

Many ways to close the bag are contemplated. In one embodiment, the disposable bag's neck can be twisted. In another embodiment, the neck of the bag can be rolled. In yet another embodiment, the neck of the bag can be clamped. Bags can be closed by rotating a lower portion of the bag relative to a stationary upper portion, or by rotating an upper portion of the bag relative to a stationary lower portion of the bag. Further, in another embodiment a user can control opening/closing the bag by using a foot pedal, a motion sensor, or a button.

Another aspect of the disclosure is directed to a visually stimulating waste disposal system directed to the positive reinforcement of infant-toddler behavior. It is commonly known that the right visual stimulation helps with a child's brain development. In a preferred embodiment, the waste receptacle features a transparent outer barrel casing and an inner barrel with a bright, colorful exterior. Further contemplated exteriors feature stop-motion animation so that upon user actuation, the receptacle features animated movements to further entice the attention of infants and toddlers. It is still further contemplated that exteriors of the inner barrel can be interchangeable for continued stimulation during a child's growth and development. Further, the enticing exteriors and the subsequent animation of the moving inner barrel can attract and train children in a positive manner to alert parents to diaper changing. The bright colors, designs, and visually stimulating images can further stimulate a child's vision and brain development.

Various objects, features, aspects and advantages of the present disclosure will become more apparent from the following detailed description of preferred embodiments of the disclosure, along with the accompanying drawings in which like numerals represent like components.

BRIEF DESCRIPTION OF THE DRAWINGS

It should be noted that the drawing figures may be in simplified form and might not be to precise scale. In reference to the disclosure herein, for purposes of convenience and clarity only, directional terms such as top, bottom, left, right, up, down, over, above, below, beneath, rear, front, distal, and proximal are used with respect to the accompanying drawings. Such directional terms should not be construed to limit the scope of the disclosure in any manner.

DETAILED DESCRIPTION OF THE DISCLOSURE

The disclosure and its various embodiments can now be better understood by turning to the following detailed description of the preferred embodiments, which are presented as illustrated examples of the disclosure defined in the claims. It is expressly understood that the disclosure as defined in the claims may be broader than the illustrated embodiments described below.

Many alterations and modifications may be made by those having ordinary skill in the art without departing from the spirit and scope of the disclosure. Therefore, it must be understood that the illustrated embodiments are set forth only for the purposes of example and that they should not be taken as limiting the disclosure as defined by the following claims. For example, notwithstanding the fact that the elements of a claim are set forth below in a certain combination, it must be expressly understood that the disclosure includes other combinations of fewer, more, or different elements, which are disclosed herein even when not initially claimed in such combinations.

Figure 1A:
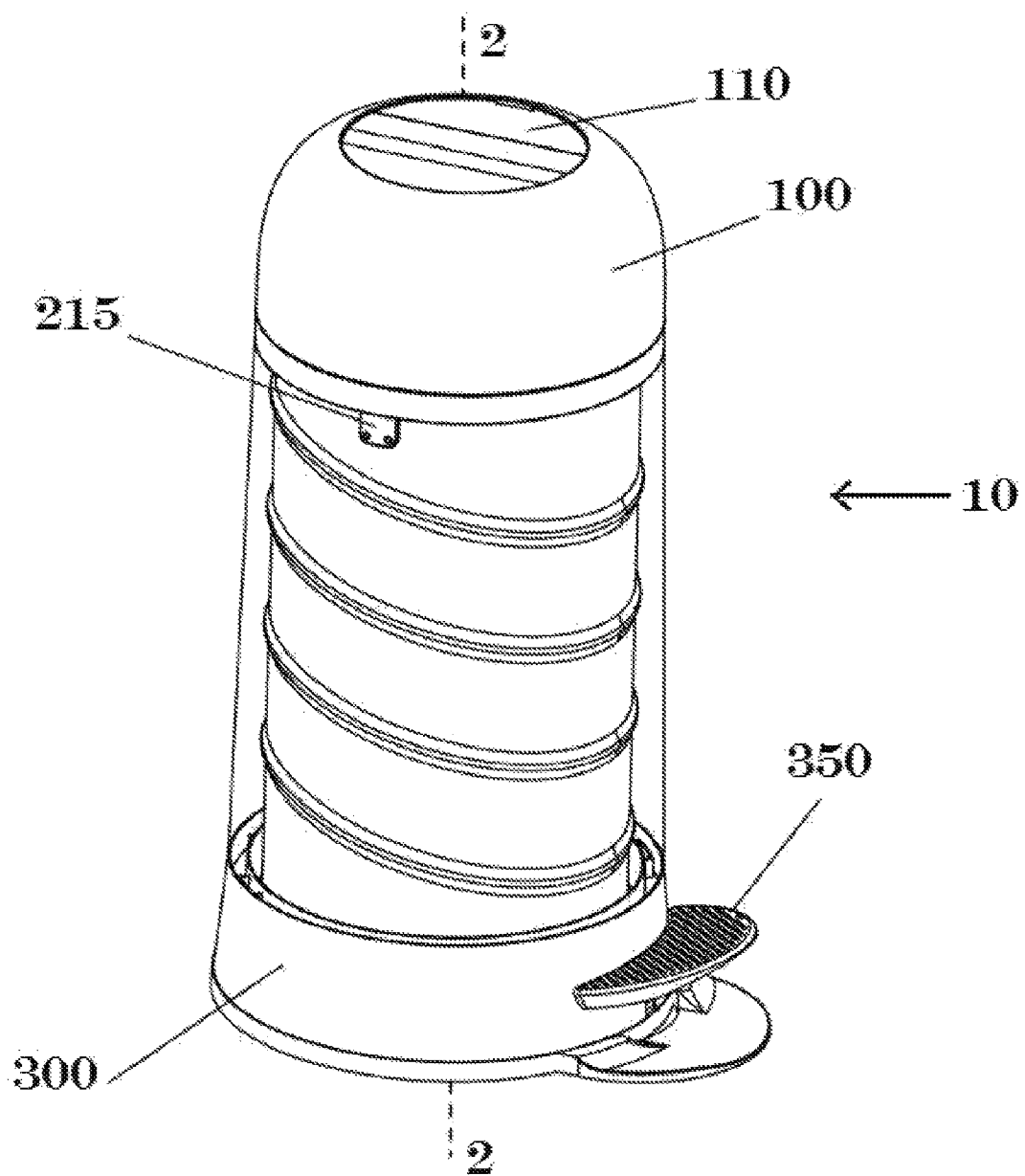
FIG. 1A is a perspective view of a first embodiment of a diaper pail having a transparent outer barrel.

FIG. 1A generally depicts one embodiment of a diaper pail or waste container assembly 10. In FIG. 1A, the container assembly 10 is shown having a base 300 with a pedal 350 protruding out of the base 300. Coupled to the base 300 is an inner barrel 210 having an inner volume and an outer barrel casing 200 enclosing/encasing the outer circumference of the inner barrel 210. There can be sufficient clearance between the inner barrel and the outer barrel so the inner barrel 210 can freely rotate without touching the outer barrel 200. The inner barrel 210 shown has some kind of spiral blade on its outside surface; this spiral blade does not aid in driving or rotating the inner barrel 210. This spiral blade does not interact nor does it engage with the outer barrel 200. Rather, the illustrated spiral blade is one of the contemplated designs on the inner barrel 210 which creates visual stimulation. In the depicted embodiment, the outer barrel casing 210 can be transparent, and the inner barrel casing 210 can be seen through the transparent outer barrel casing 200. Other contemplated embodiments feature a partly opaque outer barrel casing 200. Yet another contemplated embodiment features a completely opaque outer barrel casing 200. In the upper region of the container assembly 10 is a top 100 enclosing a top chamber. This top 100 has two transparent pivoting doors 110 that overlap each other at their terminal ends. In other embodiments, the top can have at least one pivoting door. In yet other embodiments, the top can have a door that slides open.

Although the word "barrel" usually describes a tubular object having a circular cross-sectional shape, it is specifically noted that the word "barrel" in this specification has no specific limitation or restriction on its cross-sectional shape.

Figure 1B:
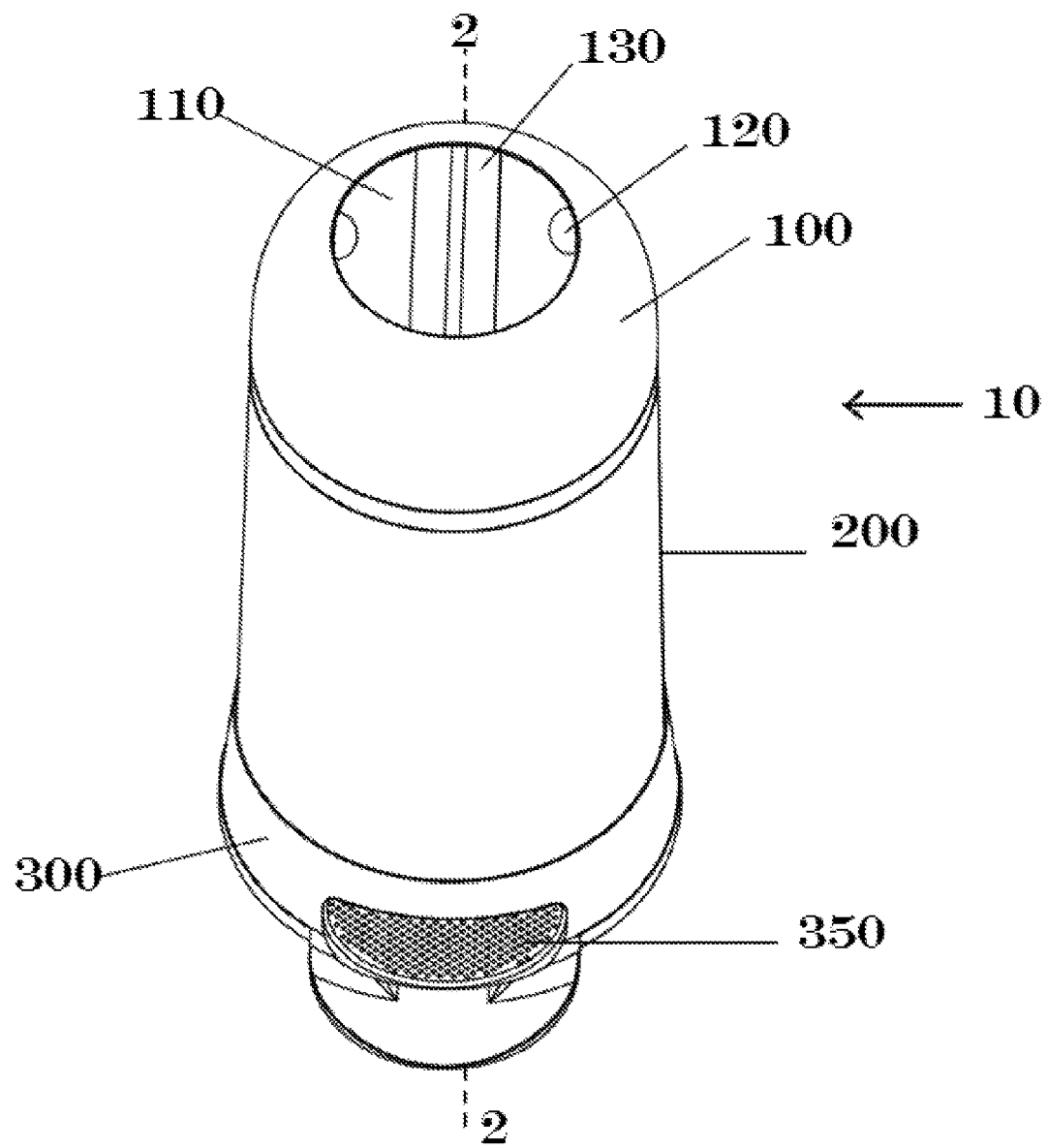
FIG. 1B is a top angled perspective view of the diaper pail of FIG. 1A (the outer barrel is not shown to be transparent, for easier illustration).

FIG. 1B shows another view of the diaper pail or waste container assembly 10. Each of the two door panels 110 is coupled to the top 100 with a resilient piece 120. The resilient piece 120 is sufficiently strong to bias the door panel 110 shut, yet it allows for the door panel 110 to swing open in a downward direction when a soiled diaper falls onto the door panel 110. After the soiled diaper passes through the door panels 110, the door panels 110 close, leaving the soiled diaper in the top chamber. In some contemplated embodiments, the resilient piece 120 can be made of silicone. In other embodiments, the resilient piece 120 can be made of any resilient material such as rubber. In further contemplated embodiments, the resilient piece 120 can be a leaf spring or a coil spring.

The embodiment in FIG. 1B shows a seal 130 between the two door panels 110. The seal 130 can keep the two overlapping door panels 110 airtight, which prevents odors from seeping out. In other contemplated embodiments, the seal 130 is a long flexible strap made of a material such as rubber, silicone, or the like attached to one or both door panels 110 at their terminal ends.

The term "door" or "door panel" refers to generally known means for a user to divide and separate space. Contemplated door or door panels of the top chamber can be selectively operated by a user. Doors or door panels of the top chamber are not limited to those that pivot on a hinge. Various different types of doors can be used. In one embodiment, the door can be shutter blades similar to those seen in cameras. Shutter blades can be operated and driven mechanically or electronically. In another embodiment, a sliding door can be used. No matter which form of door is implemented, the door can be operated via a button, a lever, or a sensor (e.g., a weight sensor, a motion sensor, a light sensor). In some embodiments, the door can be driven by a motor. In further embodiments, the door or doors are controlled by a remote controller either via a wire or wirelessly.

Figure 2:
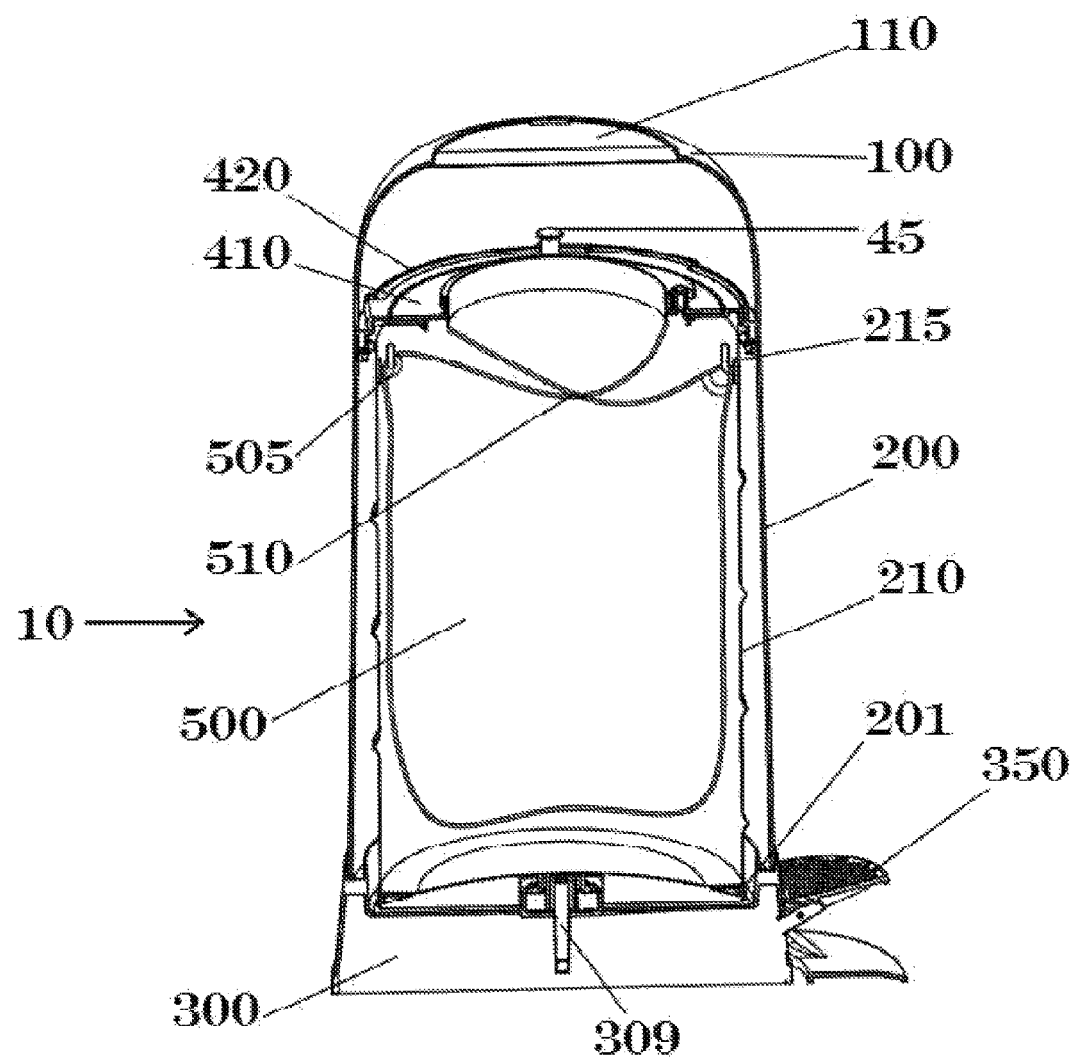
FIG. 2 is a vertical cross-sectional view taken along line 2-2 of FIGS. 1A and 1B.

FIG. 2 depicts a cross-sectional view of the container assembly 10 taken along line 2-2 of FIGS. 1A and 1B. Here, a disposable bag 500 is mounted within the waste container assembly 10, and its neck 510 is twisted closed. The bag has its top rim attached to a bag roller 410 and its shoulder regions attached to bag attachment mechanisms (e.g., hooks) on the inner barrel 210. The base 300 has a rotatable axle 309 on which a barrel base 201 of the inner barrel 210 is coupled. In one embodiment, when the foot pedal 350 is at rest, the neck 510 of the disposable bag 500 remains twisted closed. When a user steps on the foot pedal 350, the inner barrel 210 rotates in a first direction while the bag roller 410 remains stationary, thereby untwisting the neck 510 open. When the user releases his or her foot from the pedal 350, the inner barrel 210 rotates in a second direction returning the neck 510 to a twisted closed position.

It should be noted that U.S. Pat. No. 5,125,526 discloses a garbage can where the top lid opens simultaneously with an untwisting of its garbage bag. In other words, these two actions are synchronized, and for desirous reasons stated in U.S. Pat. No. 5,125,526.

The inventors of the current application, however, surprisingly discovered the advantages of the door 110 moving independently of the untwisting of the bag 500. Accordingly in one embodiment, the opening/closing of the disposable bag 500 is independent of the opening/closing of the top transparent doors 110. That is, when a soiled diaper is dropped through the doors 110, the disposable bag 500 does not open simultaneously. In another embodiment, the soiled diaper can pass through the top doors 110, stay within the top chamber, and rest atop the twisted-closed neck 510 of the disposable bag 500. The user may next step on the pedal 350 which untwists and opens the neck 510. In this way, malodorous gas does not escape from the diaper pail when the neck 510 opens and the soiled diaper drops into the bag 500. Once the pedal 350 is released, the neck 510 twists closed again.

As discussed earlier, a foot pedal 350 is only one type of contemplated actuator. Other actuators, such as a motion sensor, a weight sensor, a button, or a handle can also be used. Contemplated actuators can electronically or mechanically cause rotation of corresponding mechanisms (gears, electronic motor, rotating axle, etc.) in the base 300 which rotates the inner barrel 210. In the case of a motion sensor, a user can simply wave his/her hand or foot in front of the motion sensor to activate it, which in turn activates an electric motor in the base 300, causing the motor to rotate the inner barrel 210. Alternatively, the motion sensor can be installed on the inside of the top chamber to detect whenever the top doors 110 move, or whenever a soiled diaper enters the top chamber. In one embodiment, the diaper pail allows a few seconds of delay before an electric motor in the base 300 is activated to turn the inner barrel 210. In the case of a weight sensor, the weight sensor may be installed to detect a soiled diaper entering the top chamber and dropping onto the twisted-closed neck of bag 500. Likewise, the weight sensor can activate an electric motor in the base 300 to rotate the inner barrel 210. In another embodiment, there is provided a few seconds of delay, allowing the transparent top doors 110 to close before untwisting the neck 510.

Furthermore, in some embodiments, there can be at least 5 cm of clearance height between the top surface of the door 110 and an upper rim of the disposable bag 500 when the door 110 is closed. This allows for sufficient space to contain a soiled diaper in the top chamber. Alternatively, the clearance height can be at least 6 cm. In yet another embodiment, the contemplated clearance height is at least 7 cm. Other embodiments can have a clearance height of 10 cm and above. In an alternative embodiment, the clearance height is configured to be sufficiently tall to contain a soiled diaper between the twisted-closed neck and the door 110 of the top chamber while door 110 is closed.

One purpose of the clearance height is to essentially create a top chamber wherein a soiled diaper may stay temporarily before it is dropped into the bag 500. A preferred top chamber can be partially transparent, such as having transparent walls or doors 110 so a user may see whether or not the soiled diaper has successfully dropped into the bag 500.

The contemplated top chamber can be a clearance and confined space between a top door 110 and a closed entrance to the disposable bag 500. In the illustrated examples above, the closed entrance is the neck 510 twisted shut. Other contemplated ways to close the bag include folded shut and clamped shut. In one embodiment, rotating inner barrel 210 is not necessary because the waste container has a second set of doors as the entrance to the bag 500. This second set of doors can open/close independently of the top door 110 and can be motorized or non-motorized, controlled by a foot pedal, a button, or a sensor. In that embodiment, a soiled diaper can enter through the top door 110 and remain in the top chamber. After the top door 110 closes, the user can signal the second set of doors to open which allows the soiled diaper to fall into the bag 500.

Figure 6A:
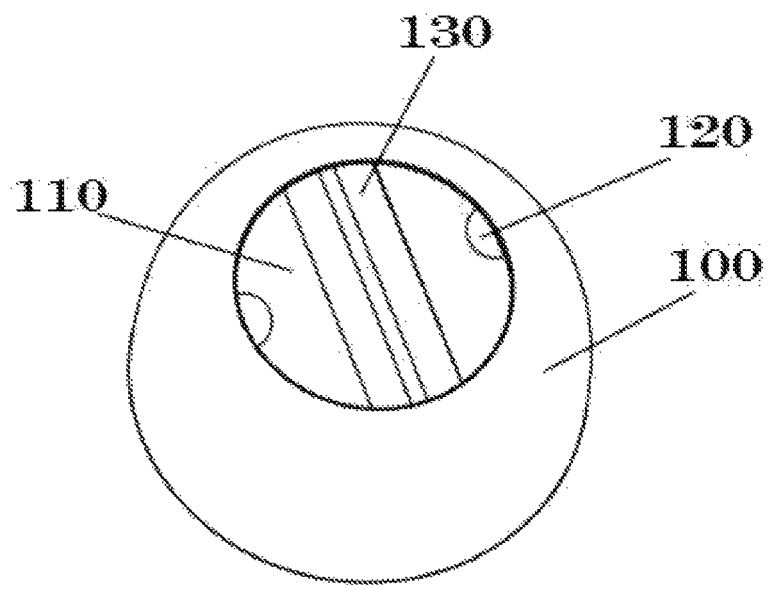
FIG. 6A is a perspective view of the top having two transparent door panels having overlapping terminal ends.
Figure 6B:
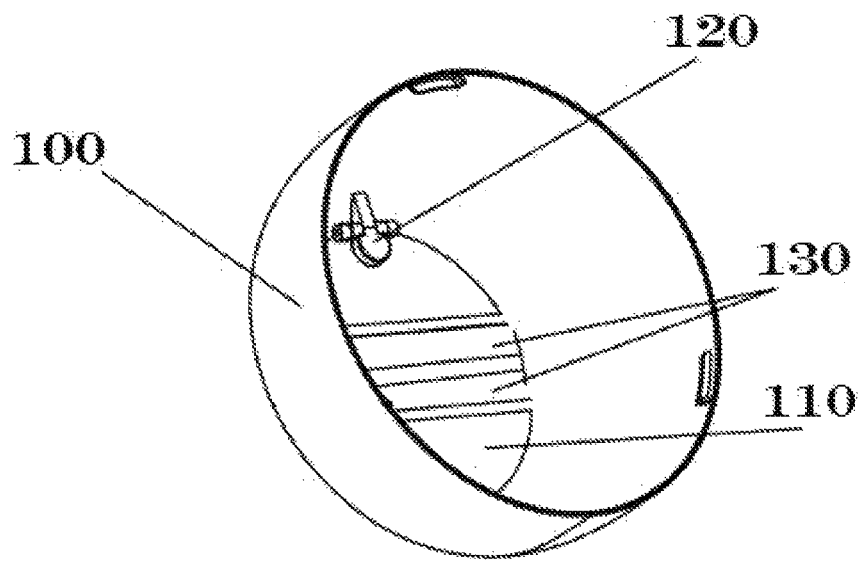
FIG. 6B is a perspective view of the inside of the top of FIG. 6A when it is turned upside down.

Transparent top doors 110 can allow a user to visually inspect the fullness of the bag 500 without encountering malodorous gas escaping. Because doors 110 are transparent, the user may simply compress the food pedal 350 and look down into the bag 500, while the top transparent doors 110 remain shut, keeping any malodorous gas in. FIGS. 6A and 6B show the top 100 of the diaper pail 10.

While the top 100 is shown as a detachable lid, many other contemplated configurations are possible. For example, the top 100 can be made as an integral part of the outer barrel 200, and the disposable bag 500 can be inserted/removed through a much larger top door 110. In another embodiment, the disposable bag 500 can be inserted/removed through a side door.

Returning to FIG. 2 with respect to bag attachment mechanisms, FIG. 2 features two hooks as a bag attachment mechanism 215 disposed on the inner barrel 210. Here, the two hooks 215 are located directly opposite one another on the inside wall of the inner barrel 210. These hooks 215 can engage with a disposable bag 500 that has receivers 505 on its shoulder region. Contemplated receiver 505 can be a hole, a sleeve, a reinforced hole, a reinforced tab, a loop, or a strip. In FIG. 2, the two receivers 505 are reinforced holes. By detachably attaching the receiver 505 of the disposable bag 500 to the inner barrel 210, the bag 500 can rotate with the inner barrel 210 (while the top rim of the bag remains stationary).

Figure 23:
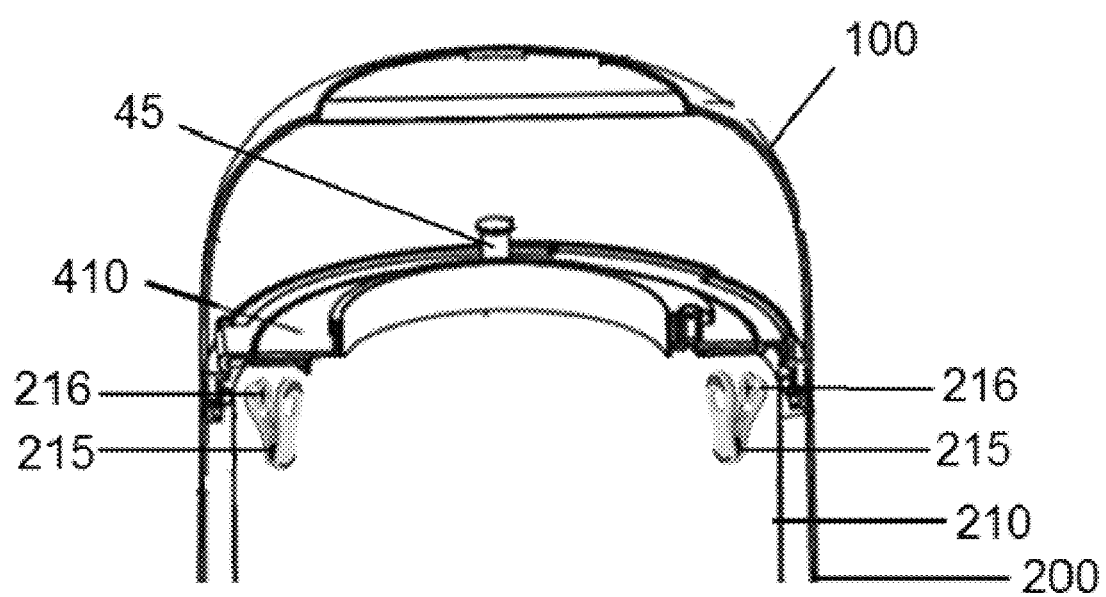
FIG. 23 shows one embodiment where the inner barrel has clips which clip onto the shoulder or body portions of a disposable bag.
Figure 24:
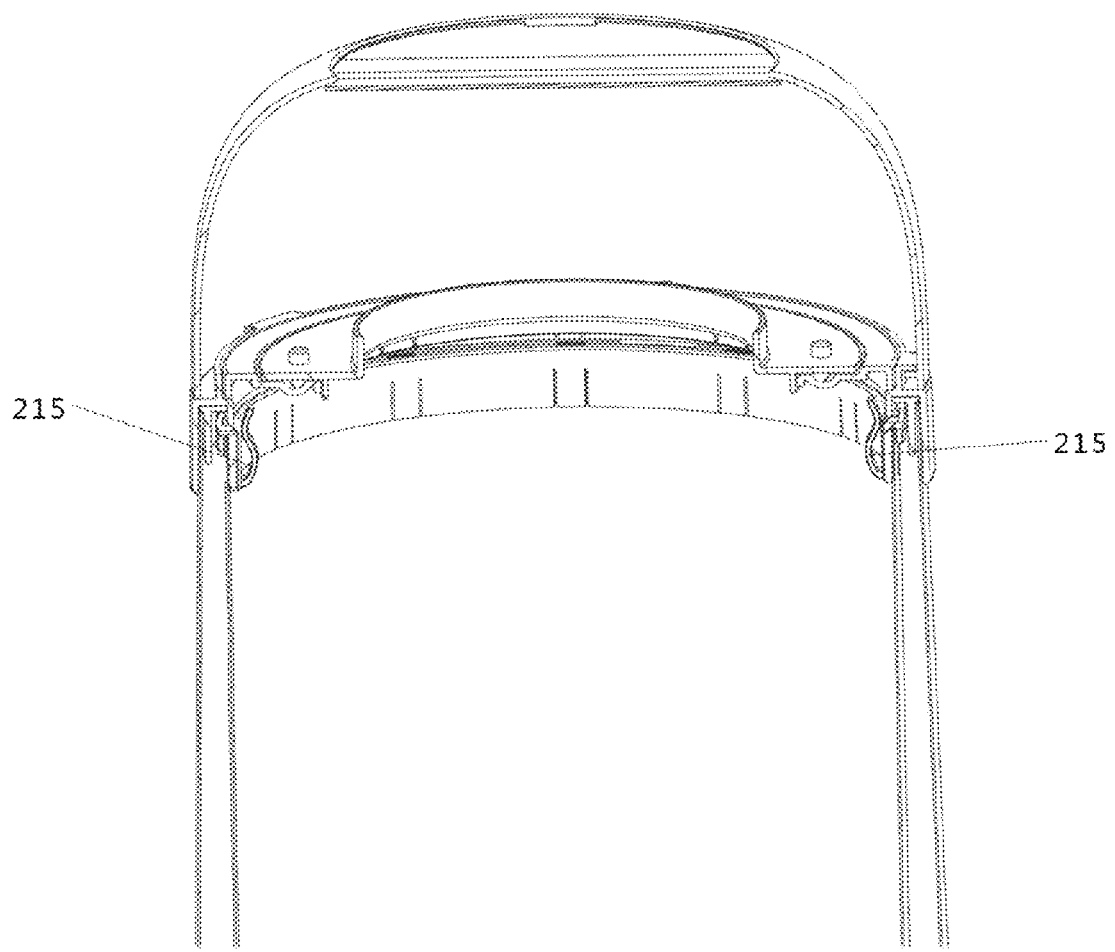
FIG. 24 shows one embodiment where the inner barrel has an additional circular collar attached to the inner barrel's top rim, and the circular collar has hooks molded into the circular collar which engage with a disposable bag.
Figure 25:
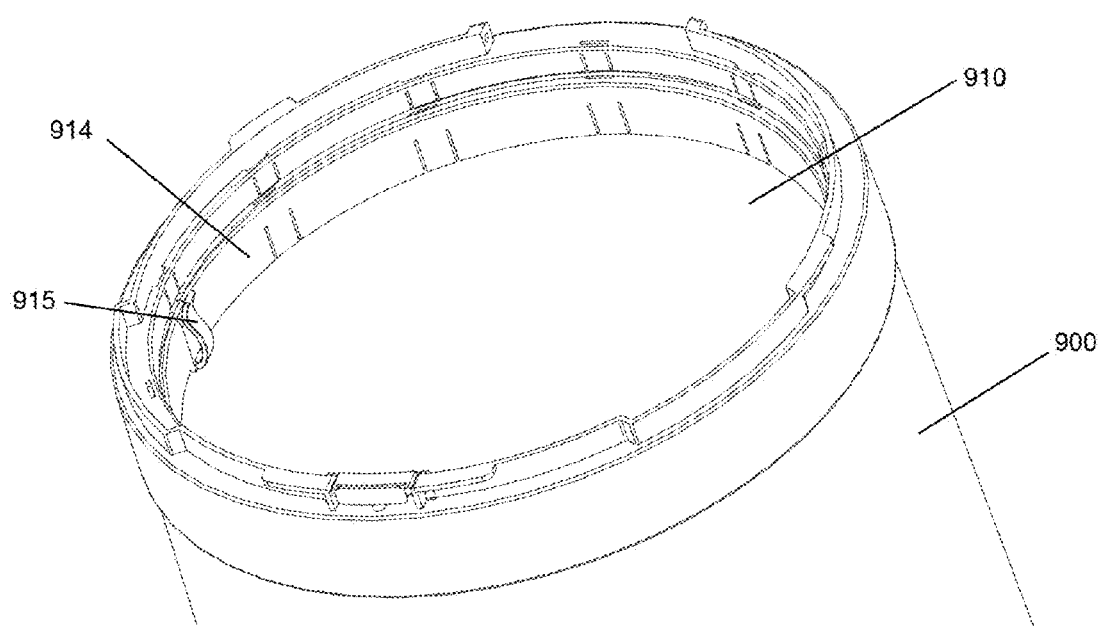
FIG. 25 is a perspective view of the inner barrel of FIG. 24 inside of an outer casing, where the top chamber and the frame assembly are removed.
Figure 26:
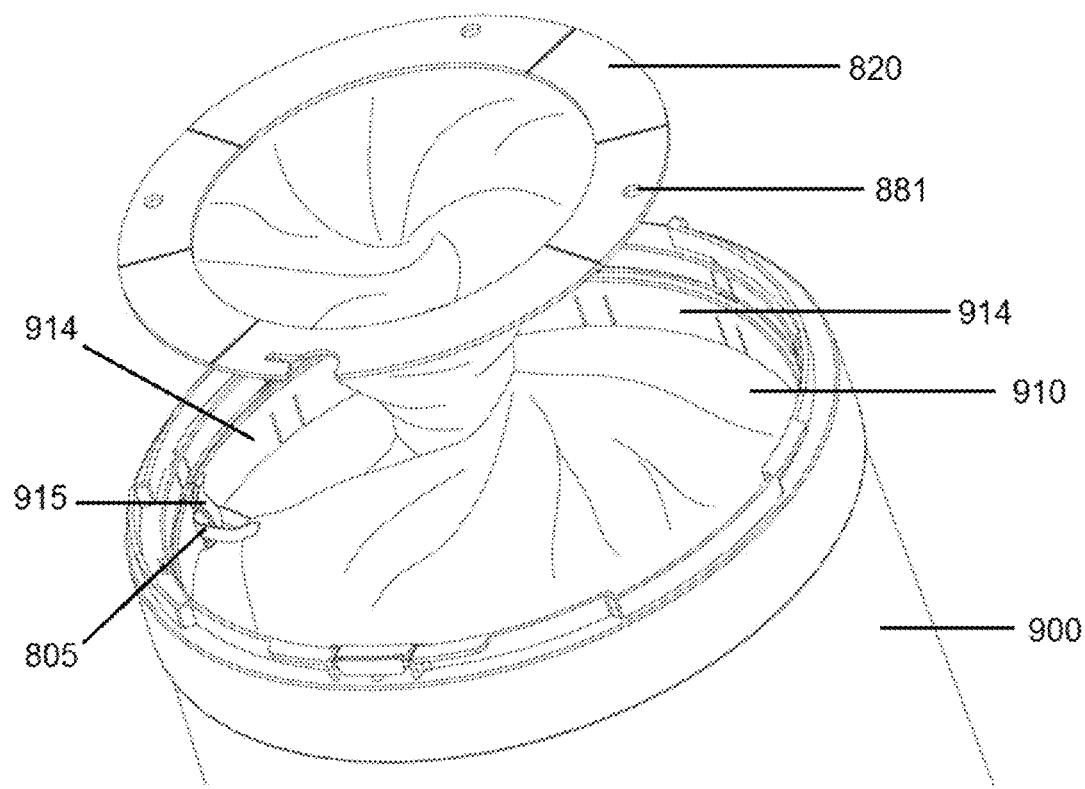
FIG. 26 is a perspective view of the inner barrel of FIG. 24 wherein the hook of the circular collar is attached to a loop on the disposable bag and the top chamber and the frame assembly are removed.

There are various ways to attach these bag attachment mechanisms 215 to the inner barrel 210. In another embodiment as illustrated in FIGS. 24, 25, 26, the inner barrel 910 is inside of an outer casing 900 and can be a flexible plastic sheet material rolled into a columnar shape. The top rims of the inner barrel 910 can be capped by a circular plastic collar 914 to keep the inner barrel 910 in its columnar shape. In another embodiment, the circular plastic collar 914 can provide a rigid attachment point for these hooks 915; without a rigid attachment point, the hooks 915 can flex inward if the hooks 915 are attached directly to the flexible inner barrel 910. With the plastic circular collar 914 in place coupled to the inner barrel 910, the torque is transmitted to the circular plastic collar 914 to rotate the bag without flexing the inner barrel 910 inward. The circular plastic collar 914 has two hooks 915 molded into the circular plastic collar 914. In FIG. 26, hook 915 is coupled to a sleeve 805 of the disposable bag. Other types of bag attachment mechanisms 215 as discussed herein can also be molded into this circular plastic collar 914. Other contemplated attachment mechanisms 215 of the inner barrel 210 can be a peg or a clip (see FIG. 23). Clips 215 can attach to the shoulder region of a bag 500 that has no corresponding receivers 505. Therefore, some embodiments of the diaper pail specifically do not require the disposable bag to have any corresponding structure for the attachment mechanism 215 of the inner barrel. In some embodiments, the diaper pail can be used with regular plastic garbage bags because the diaper pail can have attachment mechanism 215 such as the clip to clip onto a regular plastic garbage bag.

Figure 22A:
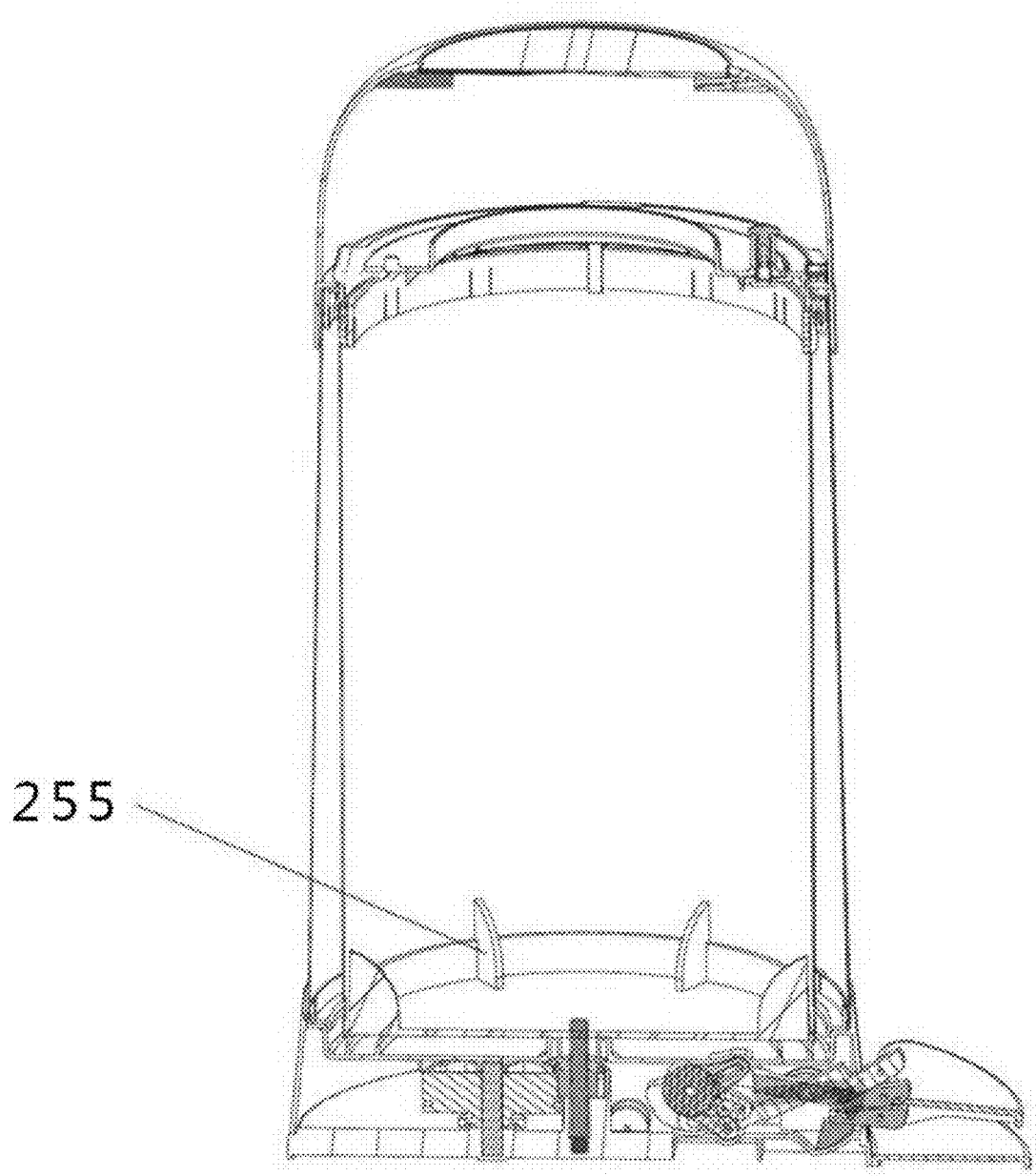
FIG. 22A shows the inner barrel having ribs which engage with the disposable bag.
Figure 22B:
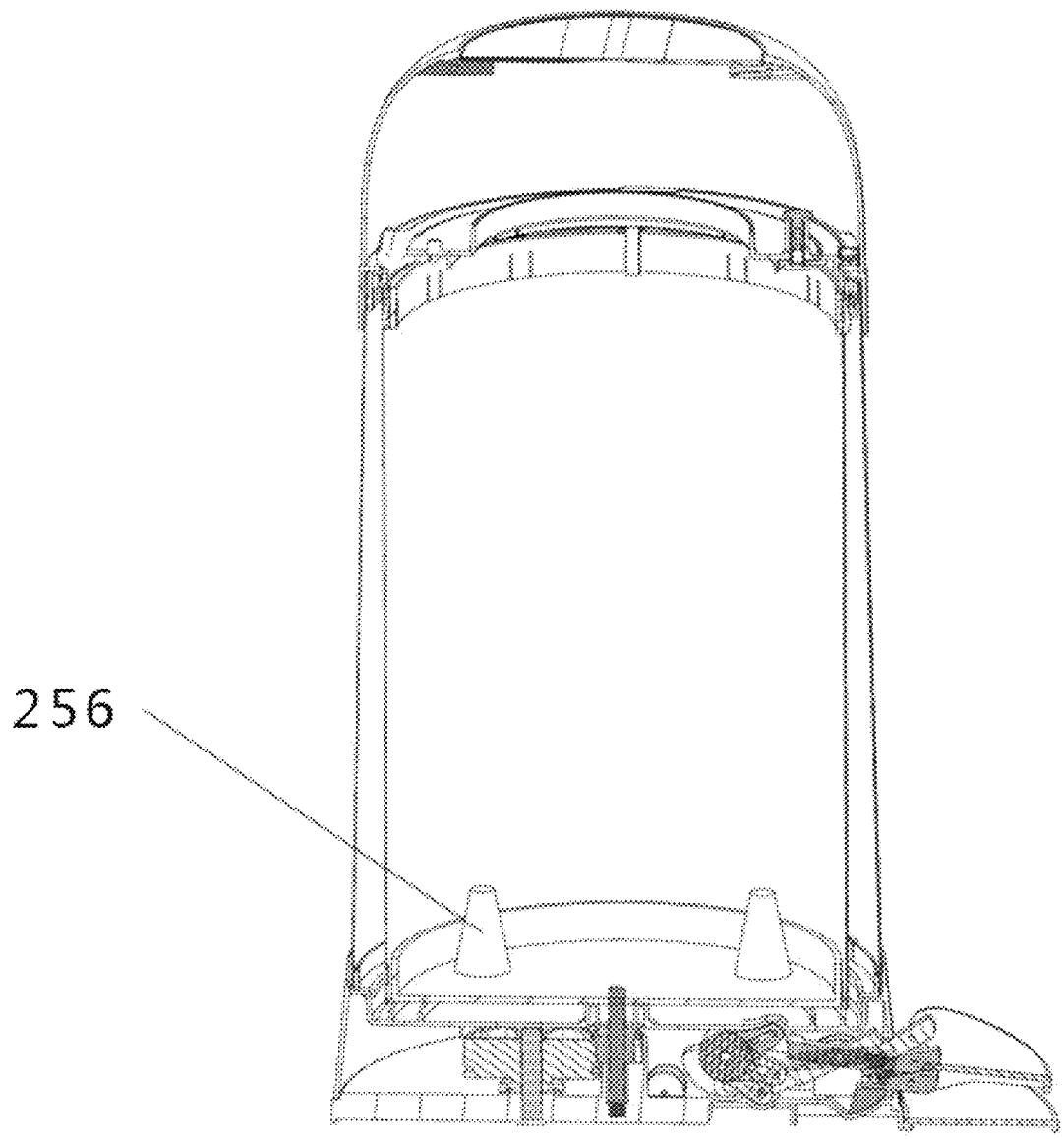
FIG. 22B shows the inner barrel having protruding bars which engage with the disposable bag.

Another way to rotate the bag along with the inner barrel is by having mechanical structures such as tentacles, ribs 255 (see FIG. 22A), protuberance 256 (see FIG. 22B), or any surface structure to enable coupling of the inner barrel 210 with the disposable bag 500.

Figure 3A:
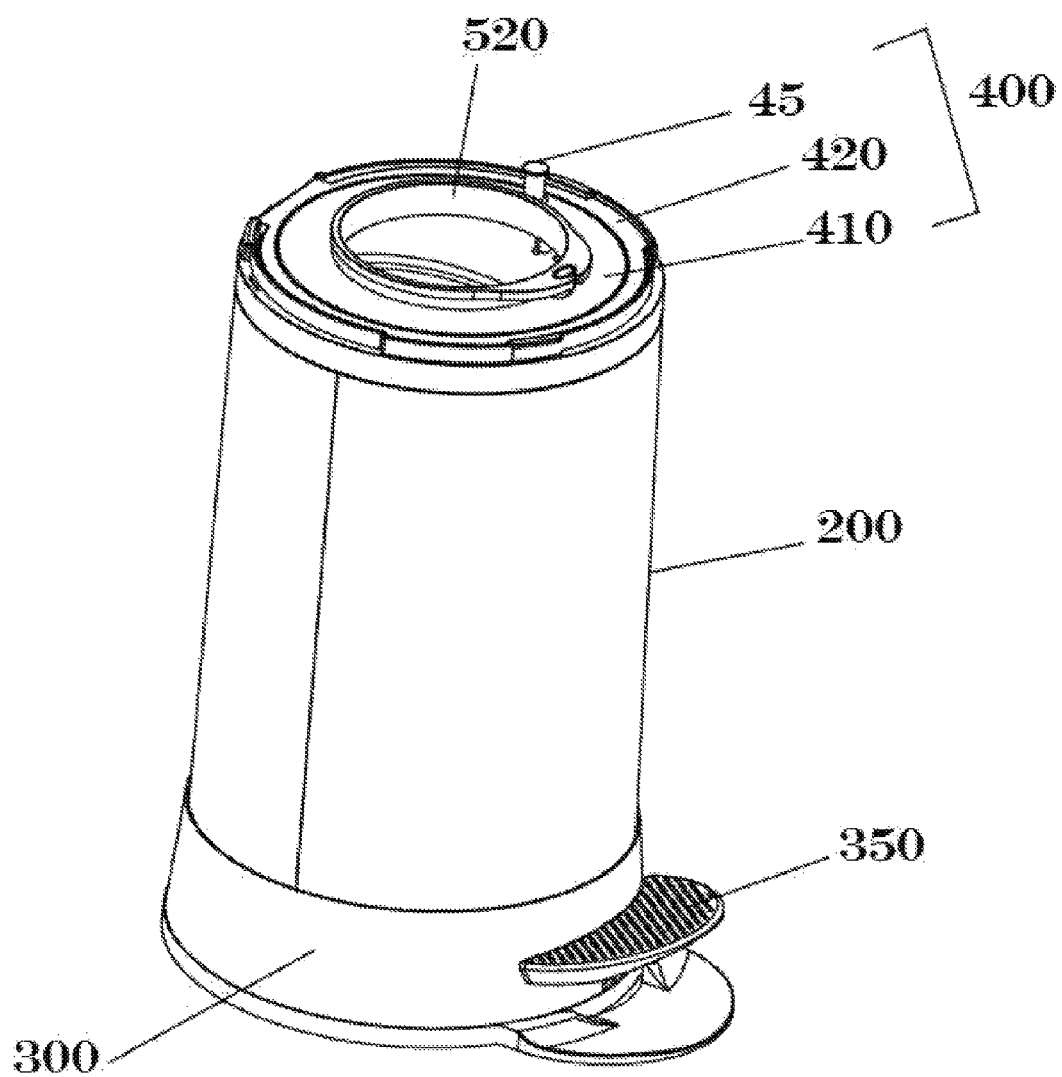
FIGS. 3A and 3B are top angled perspective views of the diaper pail of FIG. 1A with the top removed, where the bag assembly has a collar of FIG. 12B mounted on the frame assembly (the outer casing is not shown to be transparent, and the bag body is not shown).

Diaper pail 10 can have another bag attachment mechanism to couple the top rim of a bag 500 to the outer barrel casing 200. In this way, when the body of bag 500 rotates along with inner barrel 210, the top rim of the bag 500 can remain stationary along with the outer barrel casing 200. As shown in FIG. 3A, the top rim attachment mechanism can be a frame assembly 400 disposed above the inner barrel 210. In one embodiment, the frame assembly 400 does not make physical contact with the inner barrel 210. A collar 520 of the bag 500 is removably mounted onto the inner circumference of the frame assembly 400. The frame assembly 400 is comprised of a roller base 420 and a bag roller 410. The bag roller 410 can be configured to be rotated or spinned by hand, relative to the roller base 420. In the pictured embodiment, a user may pull out and hold protruding peg 45 to unlock the bag roller 410 from a first position, then manually move the protruding peg 45 in a rotating direction to rotate the bag roller 410 to a second position. Releasing of the peg 45 locks the bag roller 410 in the second position. The rotational distance between the first position and the second position is configured to be sufficient to cause the neck 510 to twist shut.

One of the purposes of the peg 45 and the bag roller 410 is for a user to preload the disposable bag 500 into a twisted-closed formation. In operation, to install a bag 500 a user would first remove or tilt open the top 100 and the frame assembly 400 from the container assembly 10. Once the inner barrel 210 is exposed, the user can place bag 500 into the inner barrel 210 and attach shoulder of the bag 500 to the bag attachment mechanism 215 on the inner barrel 210. After the bag is secured to the inner barrel 210 by means already discussed, the user can next install the frame assembly 400 back into place while the bag is entirely within the inner barrel 210. The user can next reach his/her hand through the center opening of the frame assembly 400 and pull up the collar 520 of the bag 500 through the center opening of the frame assembly 400. In the next steps the user can fasten the collar 520 of the bag 500 to the frame assembly by necessary means. Then the user can manually preload the disposable bag 500 by twisting closed its neck using peg 45 as described above.

In most embodiments, before its first use the disposable bag 500 needs to be preloaded by rotating the frame assembly 400 relative to a stationary inner barrel 210 in any of the ways already described, including manual preloading and motorized preloading. In other embodiments, the disposable bag 500 can be preloaded by rotating the inner barrel 210 relative to a stationary frame assembly 210 before its first use. For example, when a fresh disposable bag is installed into the waste container assembly 10, a user can press a button for a motor to preload the bag 500 by rotating the inner barrel 210 which forms the twisted neck 510. Thereafter, the user can press a button to rotate the inner barrel in another direction to untwist the neck 510 temporarily.

The top rim bag attachment mechanism can be designed in many ways. It can be a simple mechanical means such as hooks, pegs, or clips to grasp and fasten the top rim of bag 500 to a frame assembly 400.

Figure 3B:
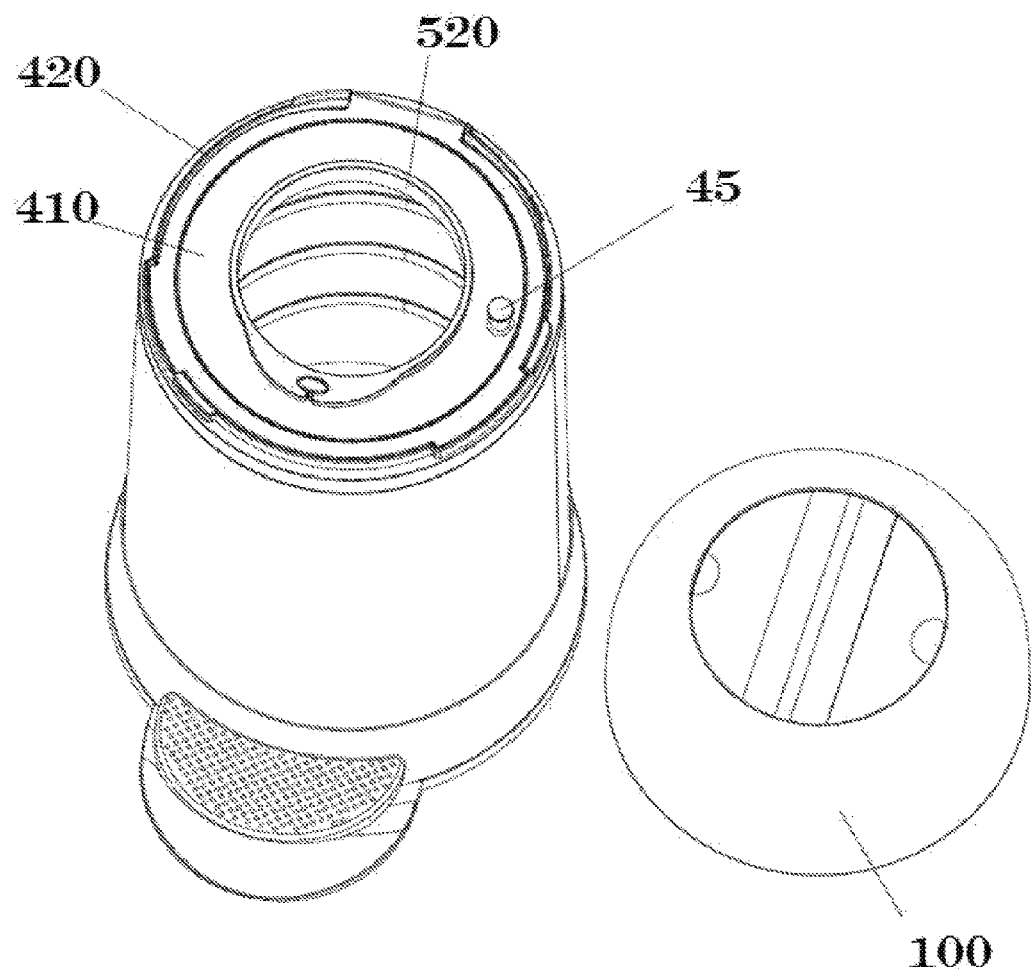
Figure 3C:
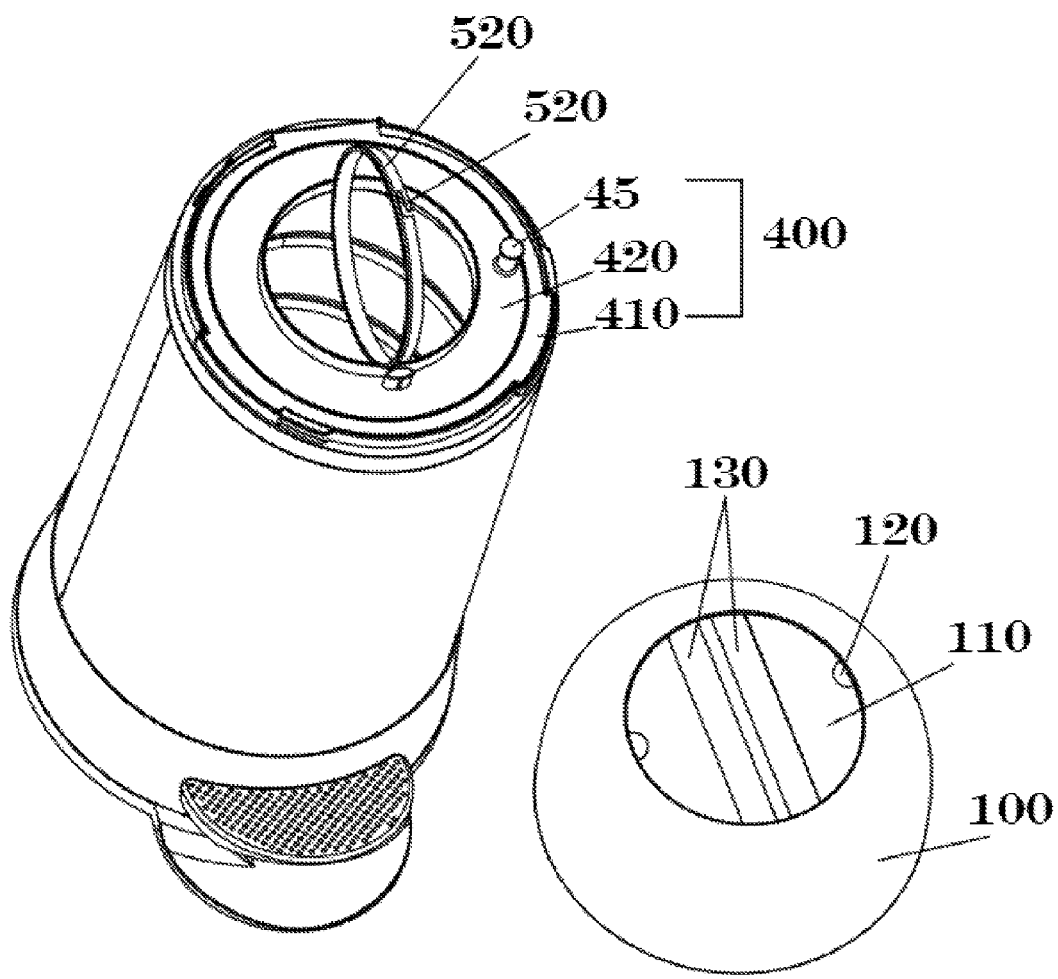
FIG. 3C is a top angled perspective view of the diaper pail of FIG. 1A with the top removed, where the bag assembly has a collar of FIG. 14B not yet mounted on the frame assembly (the outer casing is not shown to be transparent, and the bag portion is not shown).

FIGS. 3A-3C depict a diaper pail 10 with its top 100 removed for better illustration. Also in FIGS. 3A-3C, the body portion of the bag 500 is not drawn and only the collar 520 is drawn for easier illustration. Here, the frame assembly 400 is positioned above the inner barrel 210 and along the inner circumference of the upper end of the outer barrel casing 200. The top rim of the bag 500 can be a preformed collar 520 configured to detachably mount on the bag roller 410.

FIG. 3C is a perspective view of the diaper pail top 100 removed from the rest of the diaper pail 10. The bag collar 520 is sufficiently flexible to deform and fit through the opening as shown.

In another embodiment, the collar 520 can be individually provided without a permanently attached bag 500. In such embodiment, the collar 520 alone snaps into the rim of the center hole of the frame assembly 400, sandwiching the open mouth of a conventional plastic garbage bag in between.

Figure 4:
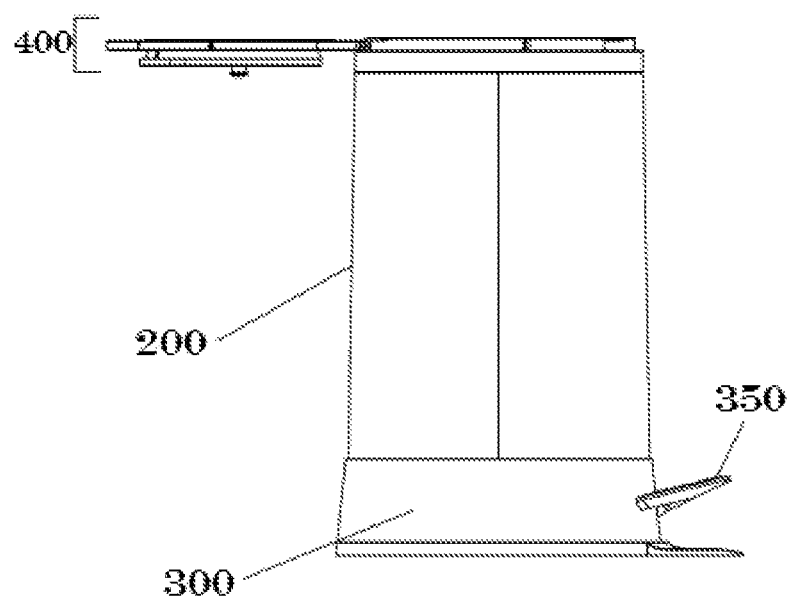
FIG. 4 is a side view of the diaper pail with the top removed and the frame assembly pivoted open.
Figure 5:
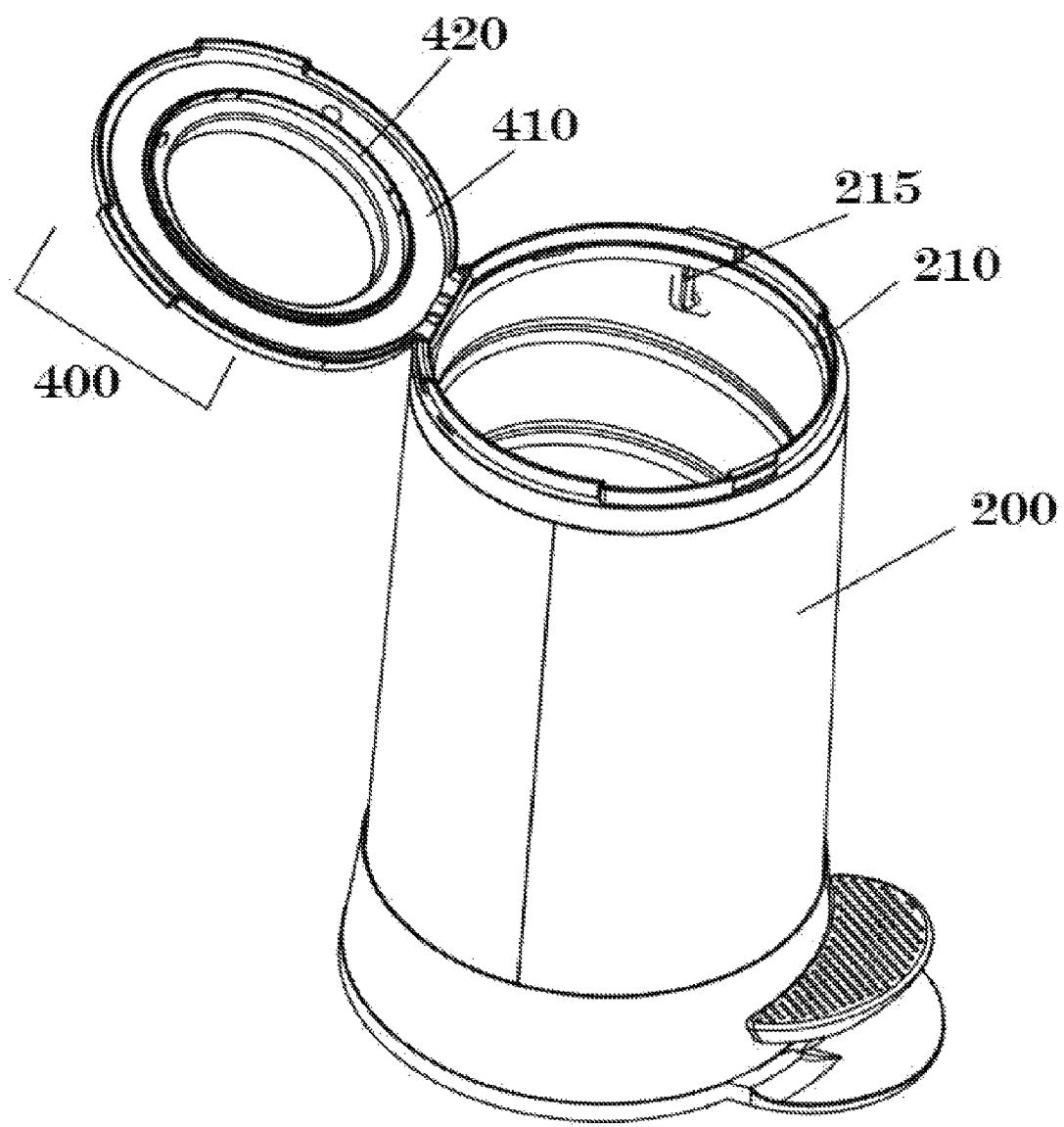
FIG. 5 is a top side perspective view of the diaper pail of FIG. 4.

FIGS. 4 and 5 show a preferred embodiment where the frame assembly 400 is pivotably coupled to the outer barrel casing 200. Here, the frame assembly 400 is pivoted open. FIG. 5 shows a close-up view of the frame assembly 400 coupled to the outer barrel casing 200 via a hinge. In another embodiment, the frame assembly 400 can be completely removed/detached from the diaper pail 10.

Additionally, FIG. 5 further illustrates a close-up view of the bag attachment mechanism 215 located on the inside of inner barrel 210. In the depicted embodiment, the attachment mechanism 215 is a hook.

FIG. 6A is a perspective view of the exterior of the top 100. FIG. 6B is a perspective view of the interior of the top 100 with the top 100 flipped upside down. Top 100 is detachably fastened to the outer barrel casing 200 by conventional methods such as being screwed on, or snapped into corresponding groves on the top rim of the outer barrel casing 200. In the pictured embodiment, the top has two pivoting transparent doors 110, each being semi-circular in shape. Each of the doors 110 is biased shut via a resilient piece 120. The resilient piece 120 is coupled to the hinges and acts as a spring, yet resiliently allows the doors to pivot open when a soiled diaper is dropped on the doors 110 based on gravitational pull, thereby providing a touch-free means to dispose of the soiled diaper. As mentioned previously, the resilient piece 120 includes and is not restricted to a spring coil, silicone or rubber piece. The resilient piece 120 must have sufficient spring tension such that after the door 110 opens, and the soiled diaper passes through, the door 110 will automatically swing back to its original position (shut).

Figure 7A:
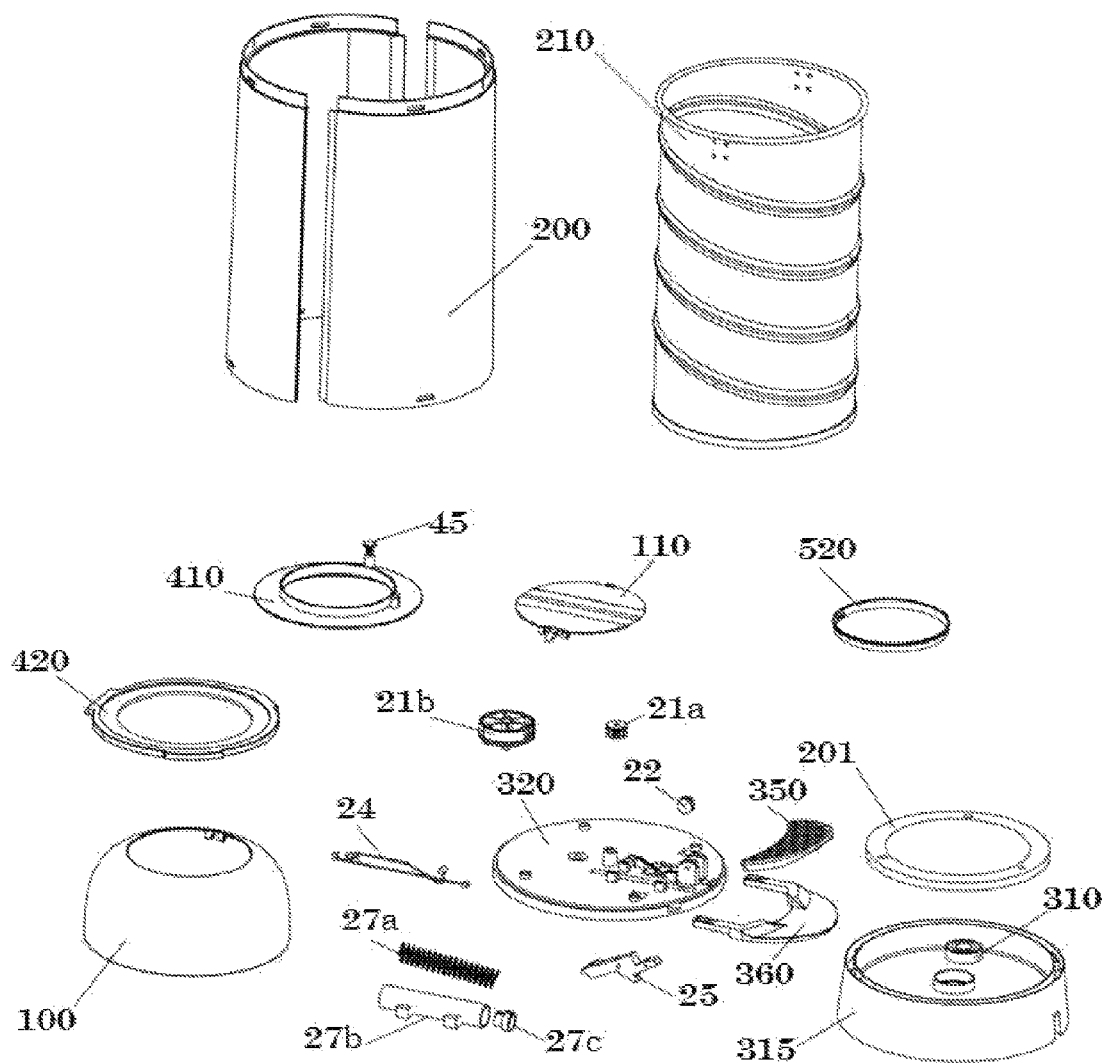
FIG. 7A is a perspective view of all of the parts of the embodiment of FIG. 1A.
Figure 7B:
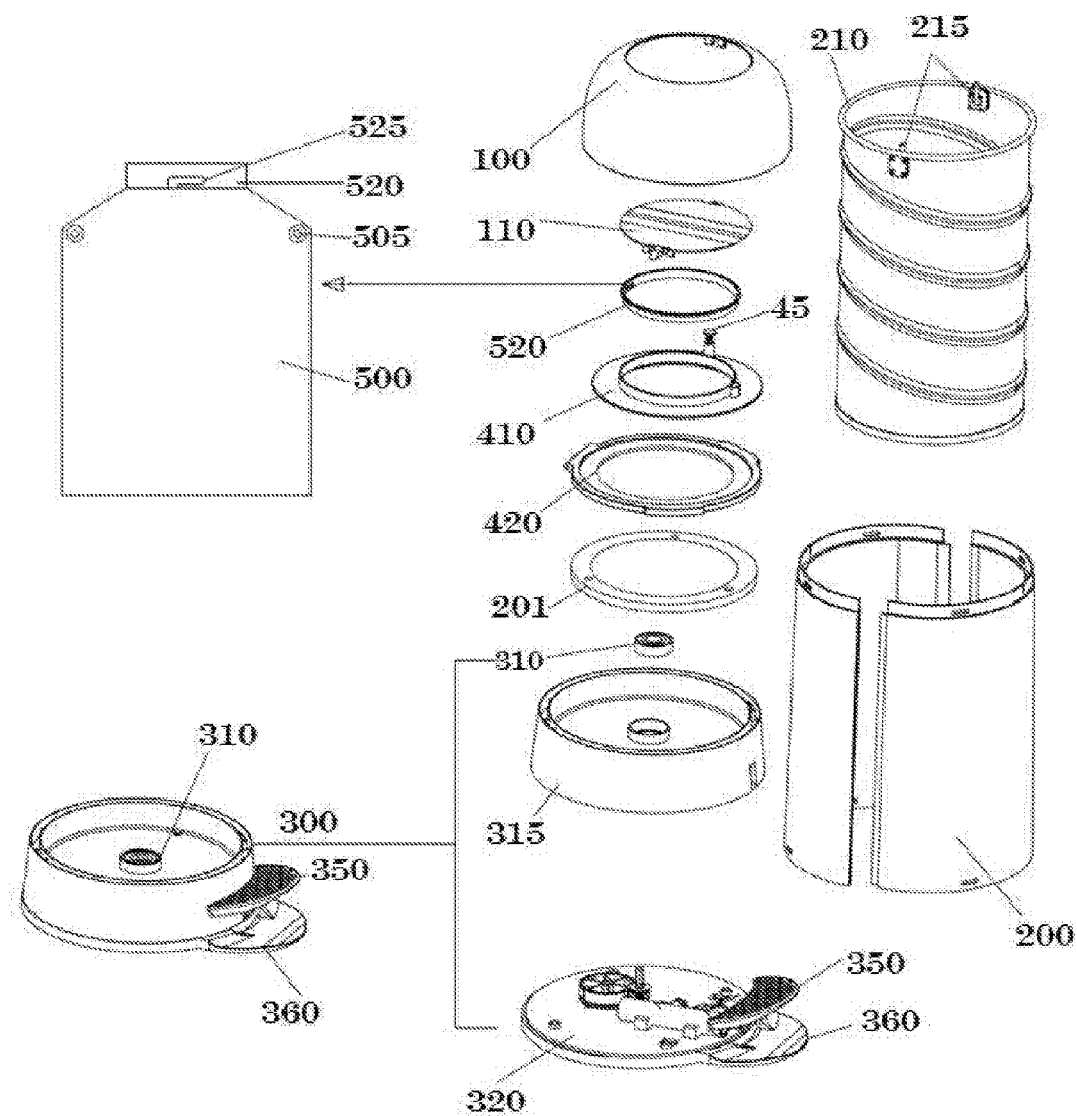
FIG. 7B is an exploded view of all of the assembly parts of the embodiment of FIG. 1A.

FIG. 7A shows the assortment of the various parts of one embodiment of the diaper pail 10. FIG. 7B is an exploded view of all of the assembly parts of the embodiment of FIG. 1A. The frame assembly 400 includes a peg 45 which fits into a housing in the bag roller 410, and the bag roller 410 rotates relative to the roller base 420. The inner barrel 210 can fit onto an inner barrel base 201 which is rotatable. The base 300 can have a rotatable axle 309 having a hexagonal cross-sectional shape, a base cover 315, a base part 320, a bracing piece 360, and a pedal 350. The inner barrel base 201 has a corresponding hexagonal female end to couple to the rotatable axle 309 so that rotation of the axle 309 would in turn rotate the barrel base 201, which would in turn rotate the inner barrel 210. In this embodiment, the outer barrel casing 200 is transparent and is coupled to the base cover 315.

Figure 8A:
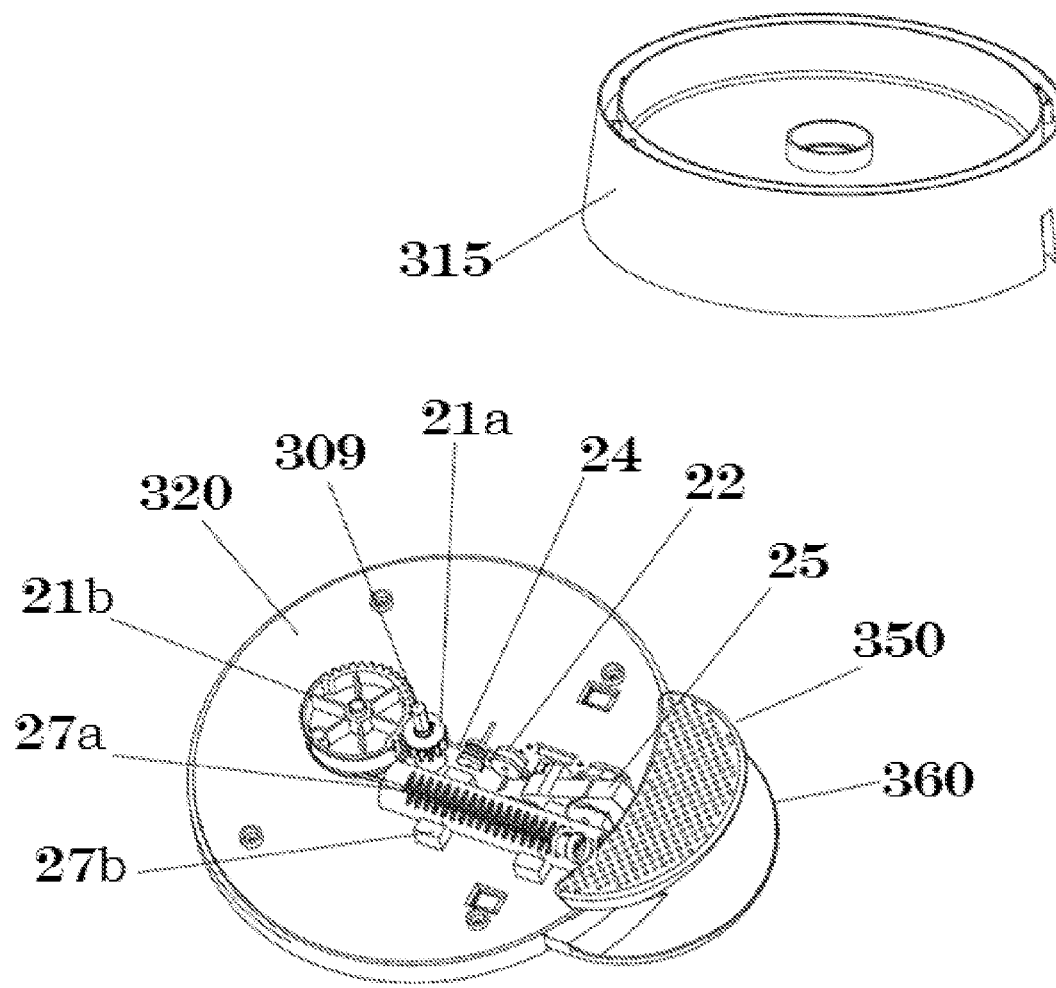
FIG. 8A is a perspective view of the inner parts of the base and the pedal of one embodiment.
Figure 8B:
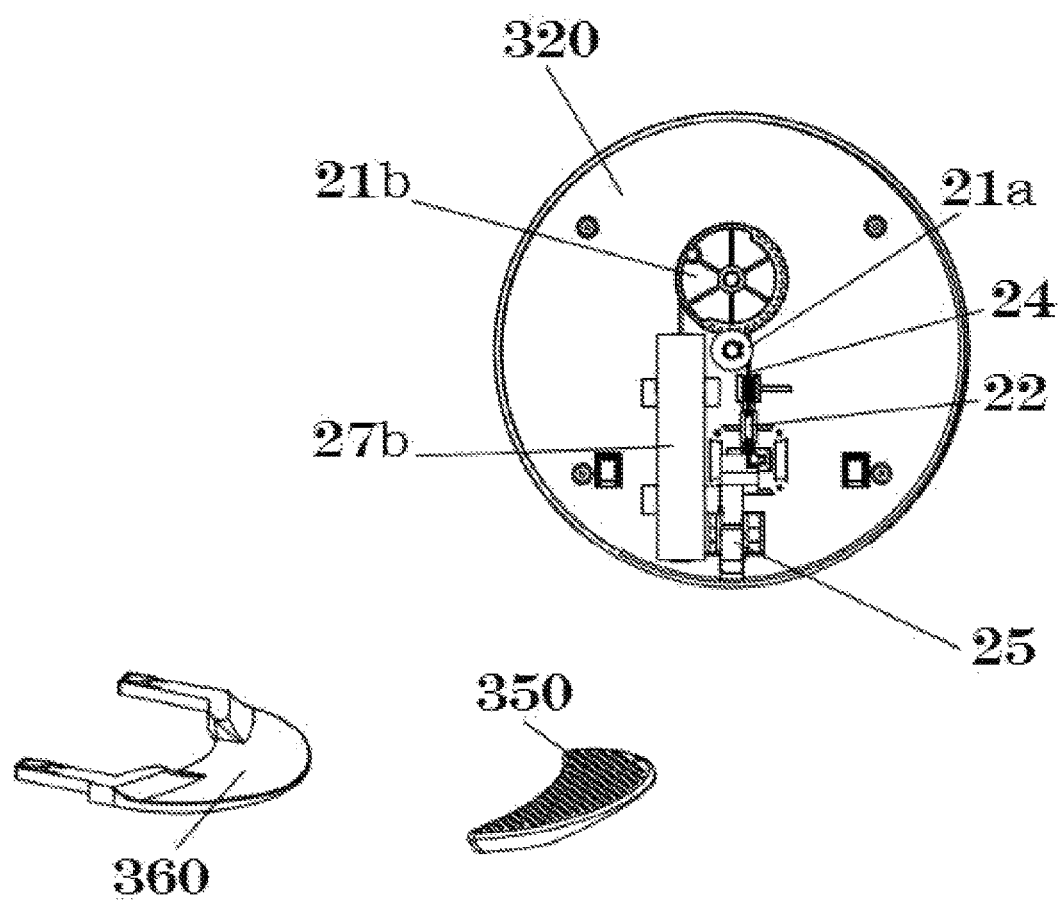
FIG. 8B is a top view of the base and perspective view of the pedal and bracing piece of the embodiment of FIG. 8A.

FIGS. 8A-8B depict close-up views of contemplated internal components in the base 300. In the embodiment shown in FIG. 8A, the base part 320 has the following components: A spring plug 27c coupled to a spring 27a, and a transparent spring cover 27b encasing both the spring plug 27c and spring cover 27b. A large gear 21b fixed on the base part 320 and coupled to a small gear 21a, which is also fixed on the base part 320. Turning of the large gear 21b would in turn rotate small gear 21a, which also turns the axle 309 which is attached to and sits on top of the small gear 21a. Additionally there is a roller 22 which acts as a pulley. A metal wire 24 is attached at one end near the base of the metal lever 25, and entrains about roller 22, and then about big gear 21b, and then enters into spring cover 27b through the center of spring 27a, and until its terminal end reaches the spring plug 27c. This terminal end is attached to the spring plug 27C. The spring 27a is fixed at its end near the gear 21B, and has a biasing force pushing the spring plug 27C in an outward direction. As the spring 27a pushes spring plug 27C outwardly, it pulls the metal wire taut. When a user steps on the foot pedal 350, it in turn presses down on the outside leg of the lever 25, causing the inside leg of the lever 25 to go up. Because this leg of the lever is in abutting contact with the metal wire 24, upward movement of this inside leg of the lever 25 also pulls on the metal wire 25 against the roller 22 to which the metal wire 24 is partially leveraged against. As the metal wire 25 begins to pull against the force of the spring 27, the metal wire 25 moves lengthwise away from the spring 27a, thereby rotates the big gear 21b. Rotation of the big gear 21b in turn rotates the small gear 21*a* and the axle 309. Although the above describes the preferred design for a base 300 which rotates the inner barrel 210, one skilled in the art would immediately recognize that other known methods and mechanisms can be implemented to achieve the same result of turning an inner barrel 210 on demand.

Figure 8C:
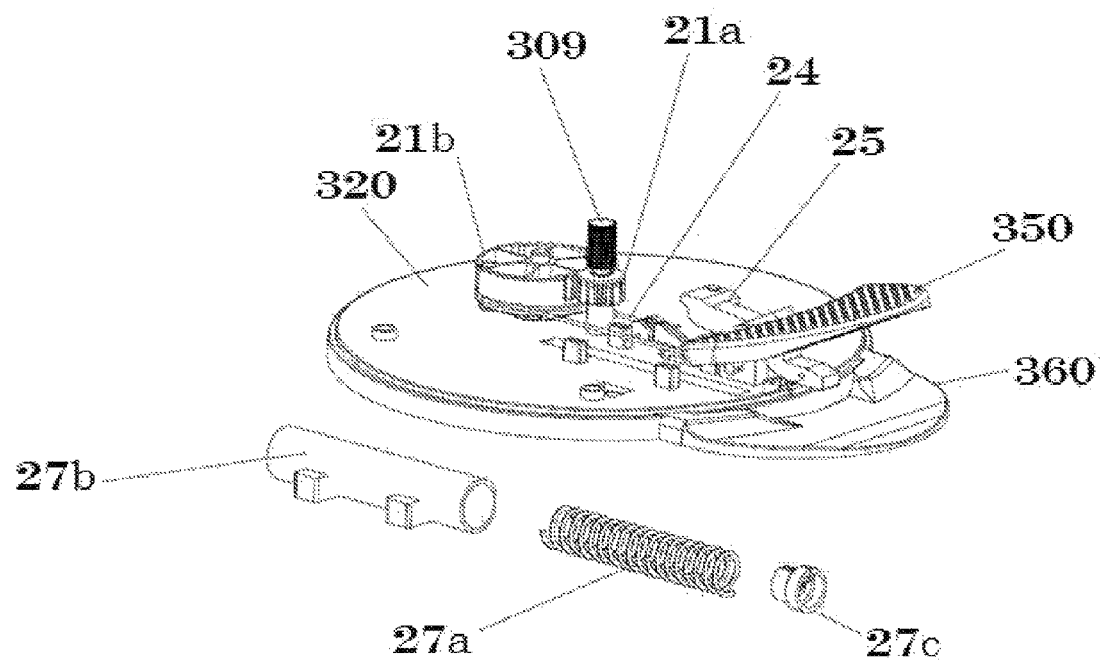
FIG. 8C is another view of the base and the pedal of FIG. 8A where the spring, spring plug, and the spring cover are taken apart.

FIGS. 8B and 8C are a top view and a perspective view of the embodiment as described above. One of ordinary skill in the art would immediately recognize that there are other known rotational mechanisms capable of turning the inner barrel 210. All other known rotational means can be implemented in any of the disclosed embodiments.

Figure 9A:
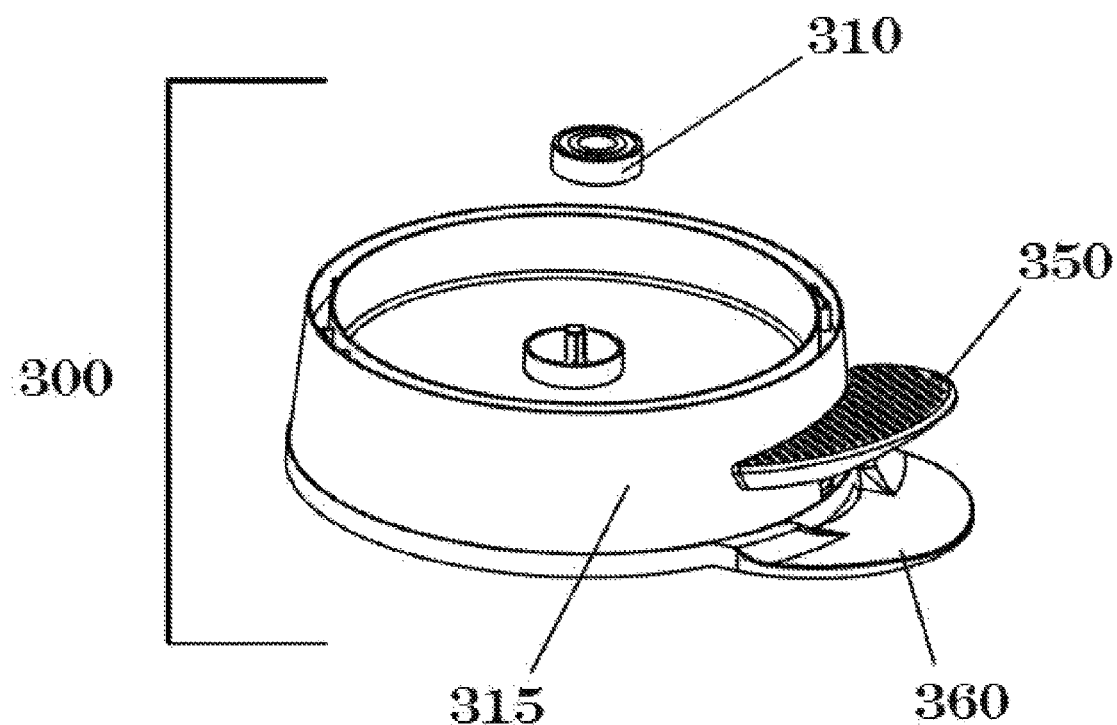
FIG. 9A is a perspective view of a first embodiment of an assembled base having a pedal where the rotating axle extends through the center.

FIG. 9A is a perspective view of a first embodiment of an assembled base 300. In one embodiment, the assembled base 300 includes a base cover 315, a pedal 350, and a bracing piece 360. Protruding out of the center of the base cover 315 is axle 309. A ball bearing 310 can be fitted around the axle 309, making rotation of the inner barrel 210 smoother. Along the upper rim of the base cover 315 is a groove to receive the outer barrel 200. In one embodiment, the outer barrel 200 fits into the groove and locks into place by rotating the outer barrel 200 clockwise.

The bracing piece 360 serves to provide sufficient leverage when compressing the pedal 350 so the diaper pail 10 does not tip over.

Figure 9B:
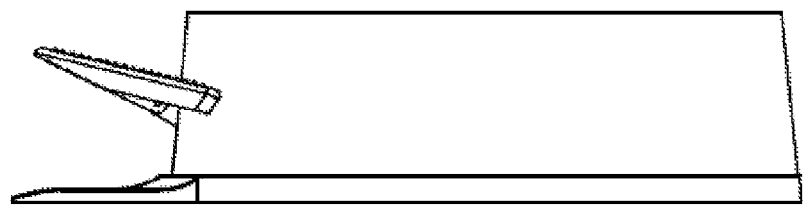
FIG. 9B is a side view of a first embodiment of an assembled base.
Figure 9C:
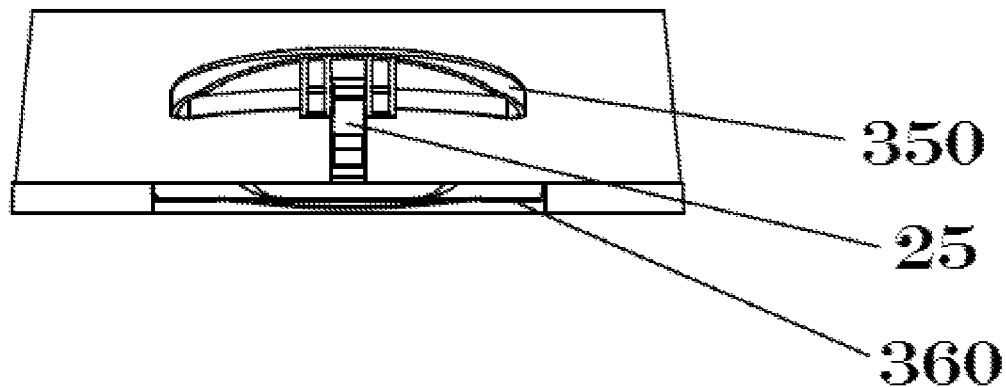
FIG. 9C is a front view of a first embodiment of an assembled base.
Figure 9D:
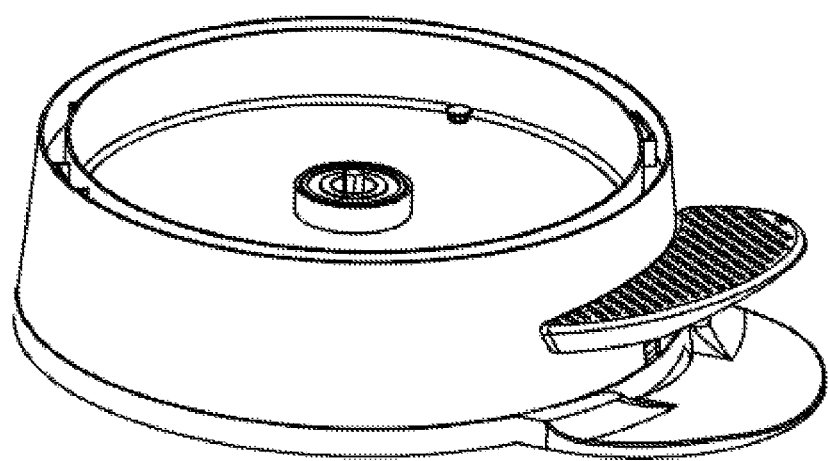
FIG. 9D is a perspective view of the base of FIG. 9A where a ball bearing is fitted around the axle, yet still allowing the rotating axle to extend therethrough.

FIGS. 9B, 9C, and 9D are different views of the base 300 of FIG. 9A.

Figure 10:
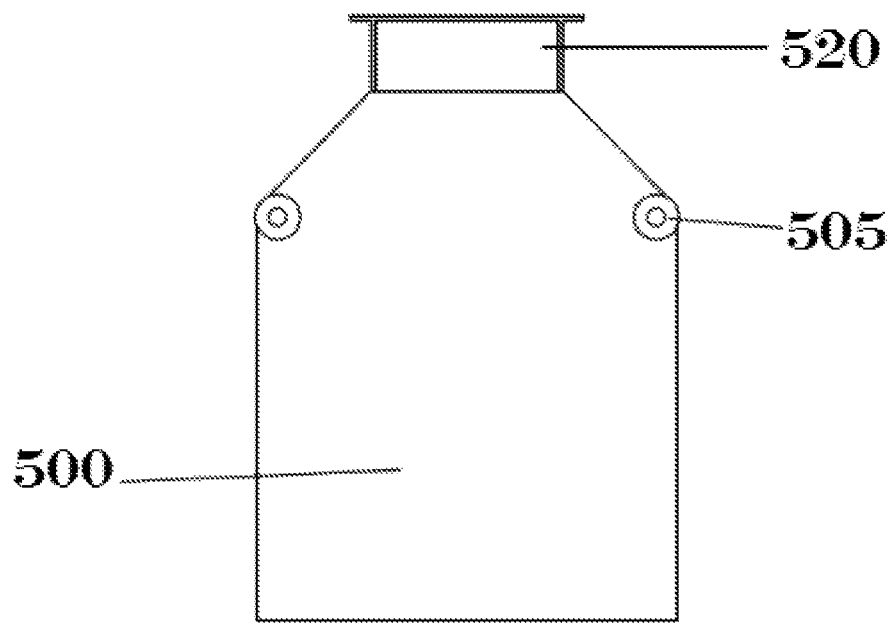
FIG. 10 is a first embodiment of a bag assembly with reinforced apertures.

FIG. 10 is a disposable bag 500 having a collar 520 permanently welded together with the bag 500. At the shoulder region are two welded/reinforced circular receivers 505, the center of which are perforated, forming a through-hole.

Figure 11:
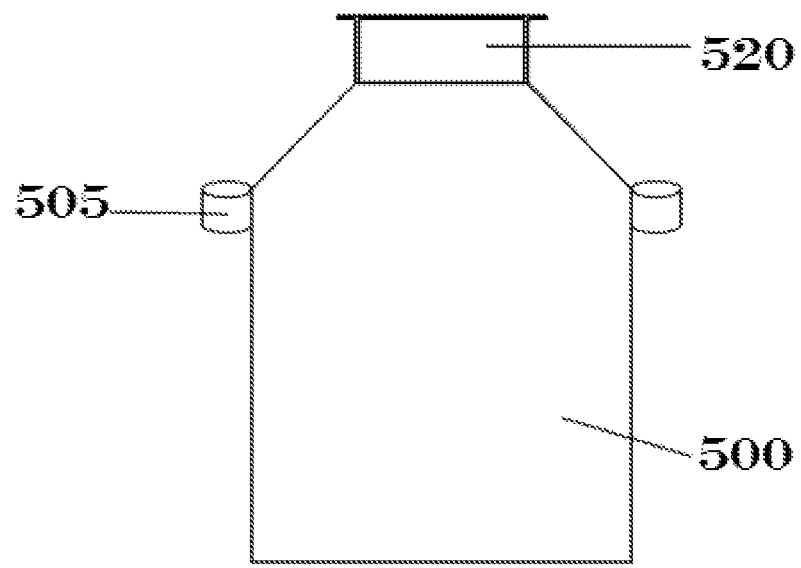
FIG. 11 is a second embodiment of a bag assembly with sleeves.

Similar to FIG. 10, FIG. 11 shows a disposable bag 500, the difference being FIG. 11 has two plastic sleeves 505 disposed on the shoulder region of the bag 500. The sleeves are for attaching the bag 500 to corresponding bag attachment structures on the inner barrel 210.

Figure 12A:
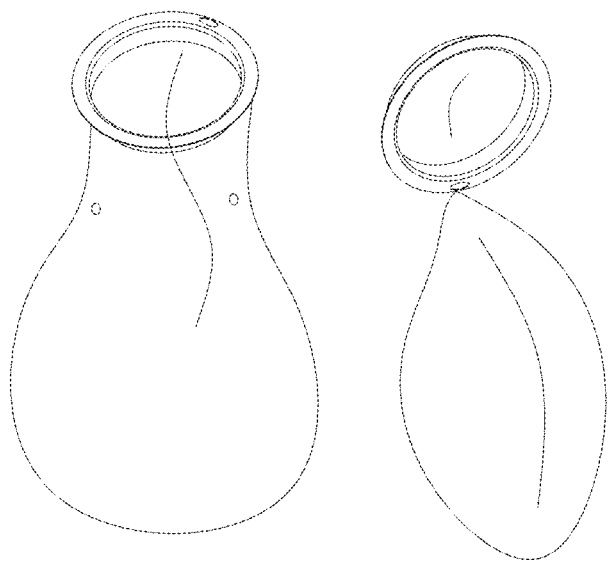
FIGS. 12A-12B show one embodiment of a bag assembly with one type of collar.
Figure 12B:
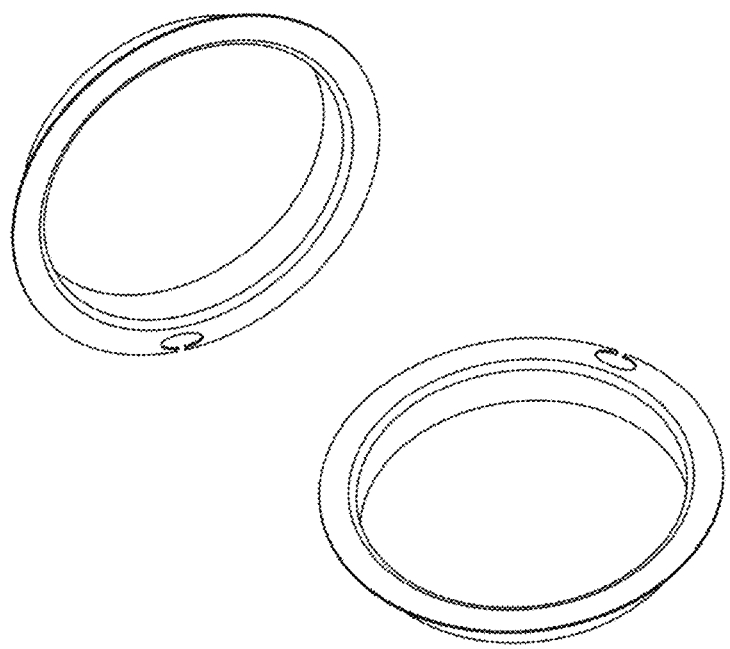

FIGS. 12A-12B show a bag assembly 500 having one type of collar 520.

Figure 13A:
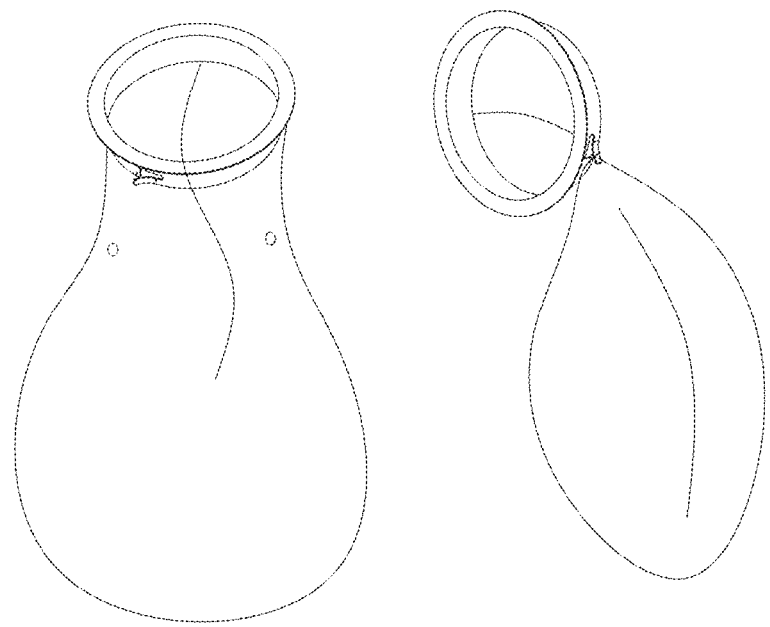
FIGS. 13A-13B show another embodiment of a bag assembly with another type of collar.
Figure 13B:
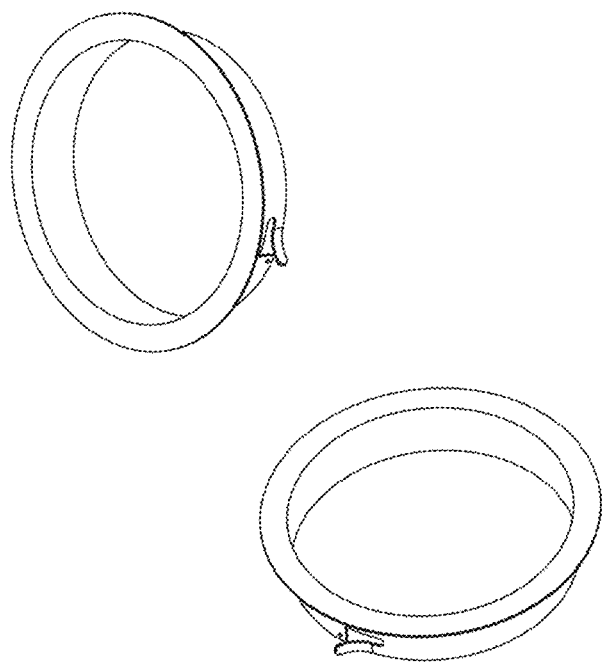

FIGS. 13A-13B show a bag assembly 500 having one type of collar 520.

Figure 14A:
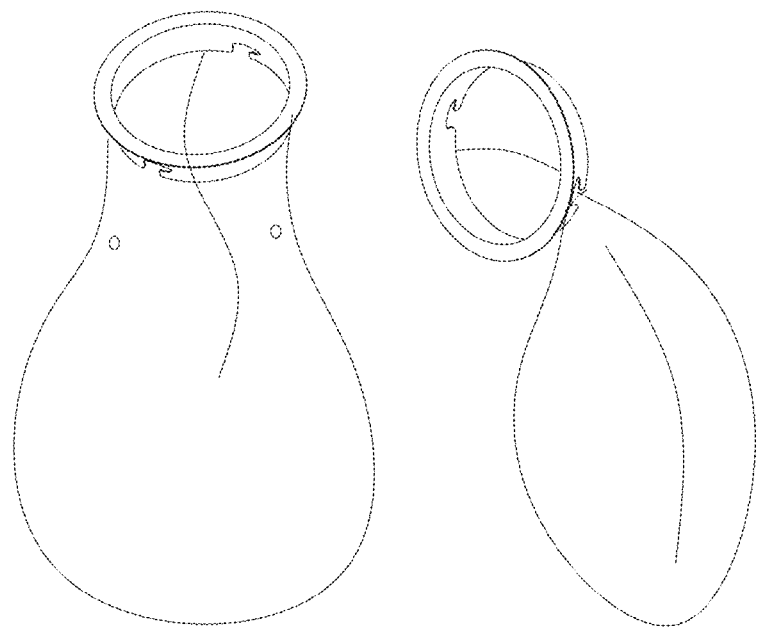
FIGS. 14A-14B show another embodiment of a bag assembly with another type of collar.
Figure 14B:
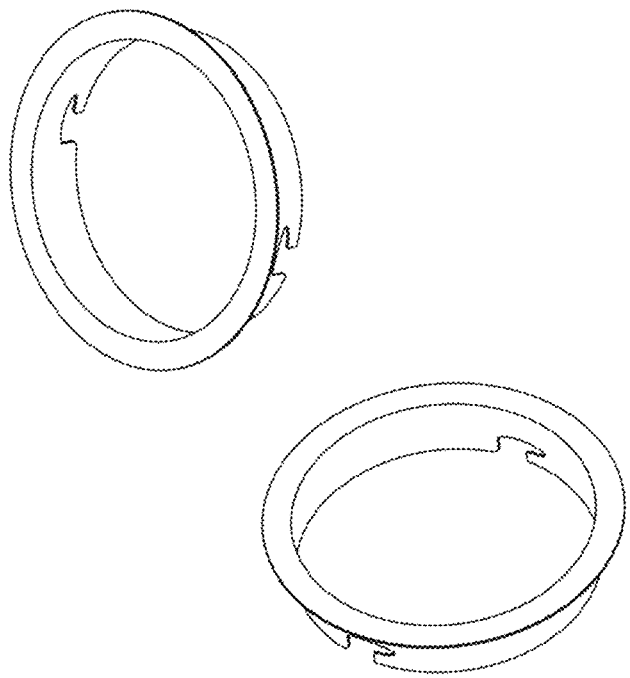

FIGS. 14A-14B show a bag assembly 500 having one type of collar 520.

Figure 15A:
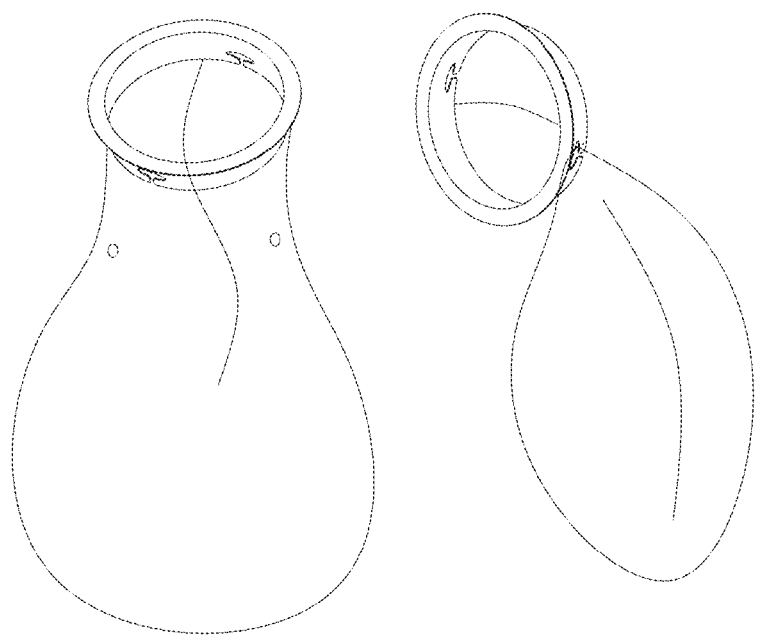
FIGS. 15A-15B show yet another embodiment of a bag assembly with yet another type of collar.
Figure 15B:
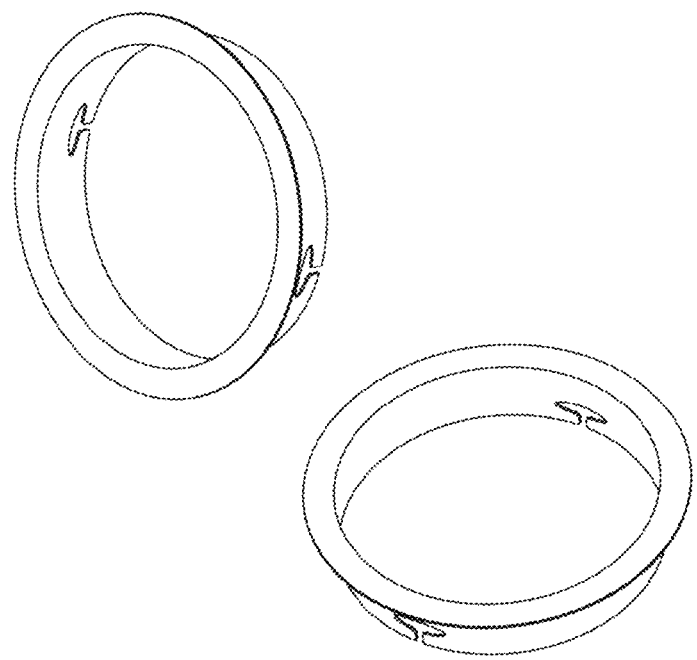

FIGS. 15A-15B show a bag assembly 500 having one type of collar 520.

While the above description in general describes embodiments where the bag 500 is twisted closed by using a rotating inner barrel, one skilled in the art would immediately recognize a variety of ways to implement the inventive subject matter without twisting the neck 510 of a bag 500.

Figure 16:
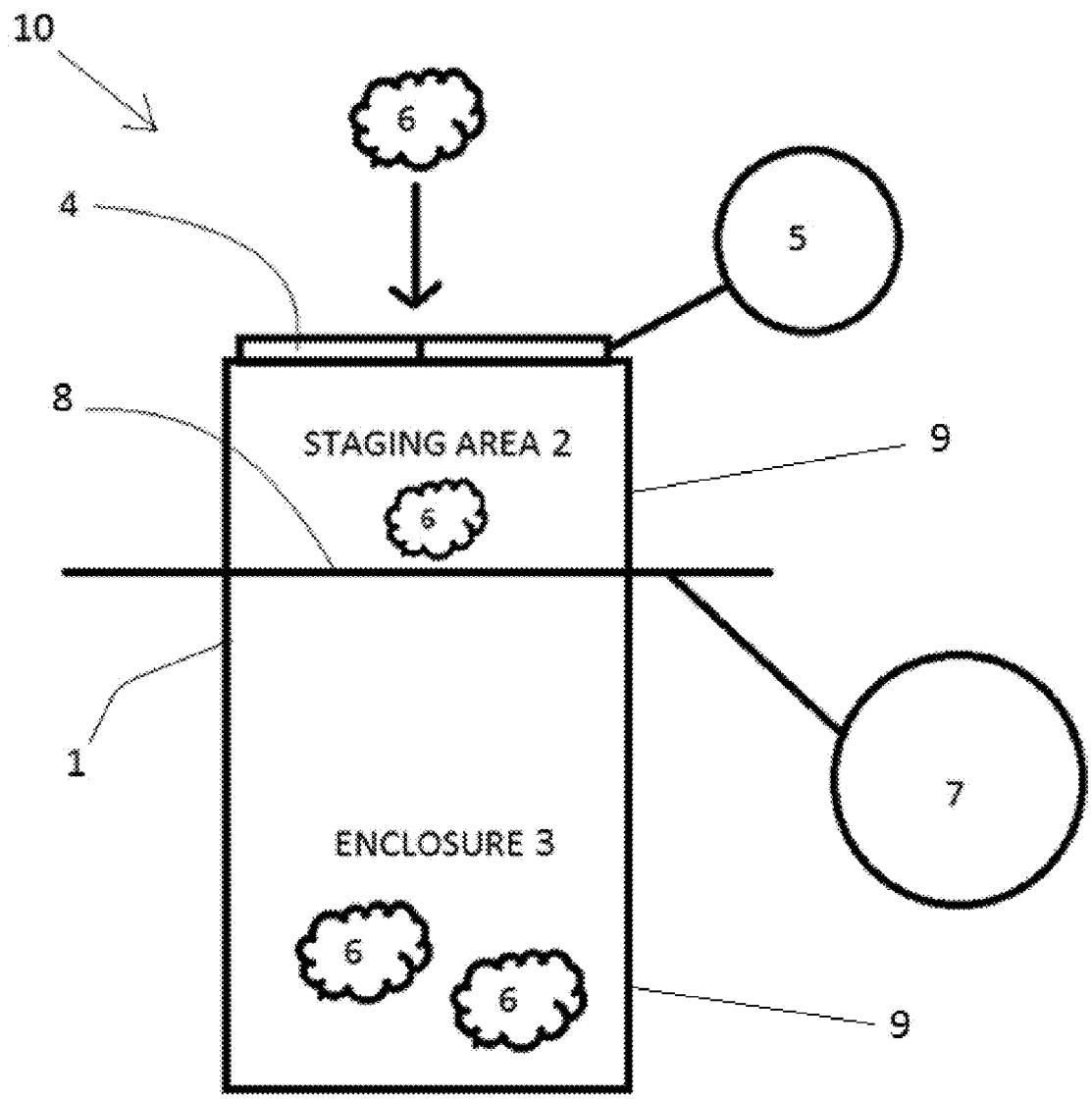
FIG. 16 illustrates a generalized embodiment.

Referring now to FIG. 16 in a more generalized embodiment, a waste disposal system 10 has an enclosure 3 to hold waste material 6. The enclosure 3 can be simply an empty space inside of the container assembly 1. In one embodiment, the enclosure 3 is a disposable bag. In another embodiment, the enclosure 3 is a bucket that fits inside or under the container assembly 1.

The container assembly 1 has a top door 4 and an actuator 5 to control the opening and closing of the top door 4. This actuator 5 can be any known mechanical, electrical, or magnetic type of controller. It can be as simple as a rubber spring as described above, or as complicated as a motorized unit controlled by a motion sensor to sense a user waving his/her hand to open the top door 4.

The container assembly has a staging area 2 to temporarily hold a waste material for reasons already described. In one embodiment, the staging area is an enclosed clearance space between the top door and the entrance 8 to the enclosure 9. In another embodiment, this clearance space is at least 10 cm.

There is an entrance 8 to the enclosure 3, and the opening/closing of the entrance 8 is independently controlled by actuator 7. The opening/closing of the entrance 8 is independent of the opening/closing of top door 4. Control of actuator 7 can be done with a foot pedal and a rotating inner barrel as already described to twist shut the neck 510 (i.e., entrance 8) of a bag 500. In another embodiment, the actuator 7 can involve a motorized unit that selectively opens and closes another set of doors (i.e., entrance 8) upon the pressing of a button, stepping on a button, or movement in front of a motion sensor.

In yet another embodiment, a bag 500 can be used as an enclosure 3, and the bag does not twist within the container assembly 10. Instead, a neck of the bag is deformed by mechanical arms to essentially close its neck. In another embodiment, some kind of cinching ring or shutter blades can be used to cinch the neck of the bag closed. In a further embodiment, the inner barrel 210 does not rotate, and the twisting/untwisting of the neck 510 can be done by a motorized rotatable bag roller 410.

Figure 17:
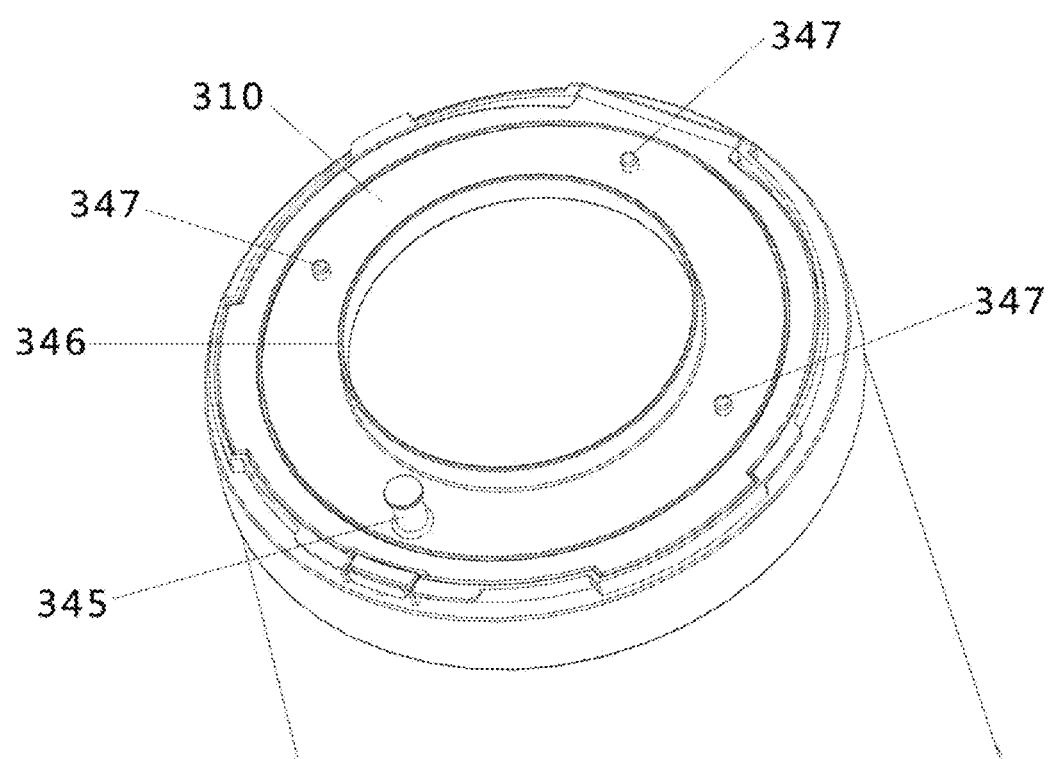
FIG. 17 shows another embodiment of the frame assembly having three protruding stubs as couplers.
Figure 18:
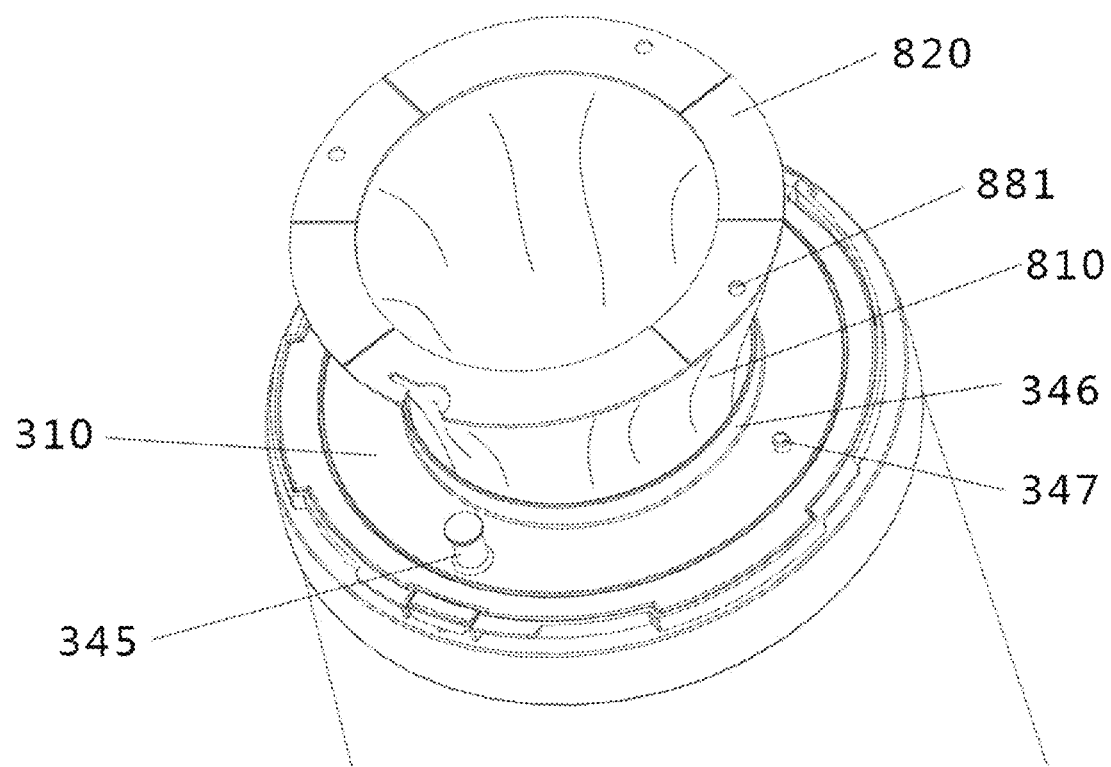
FIG. 18 shows a disposable bag having a foldable collar being installed onto the frame assembly of FIG. 17.
Figure 27:
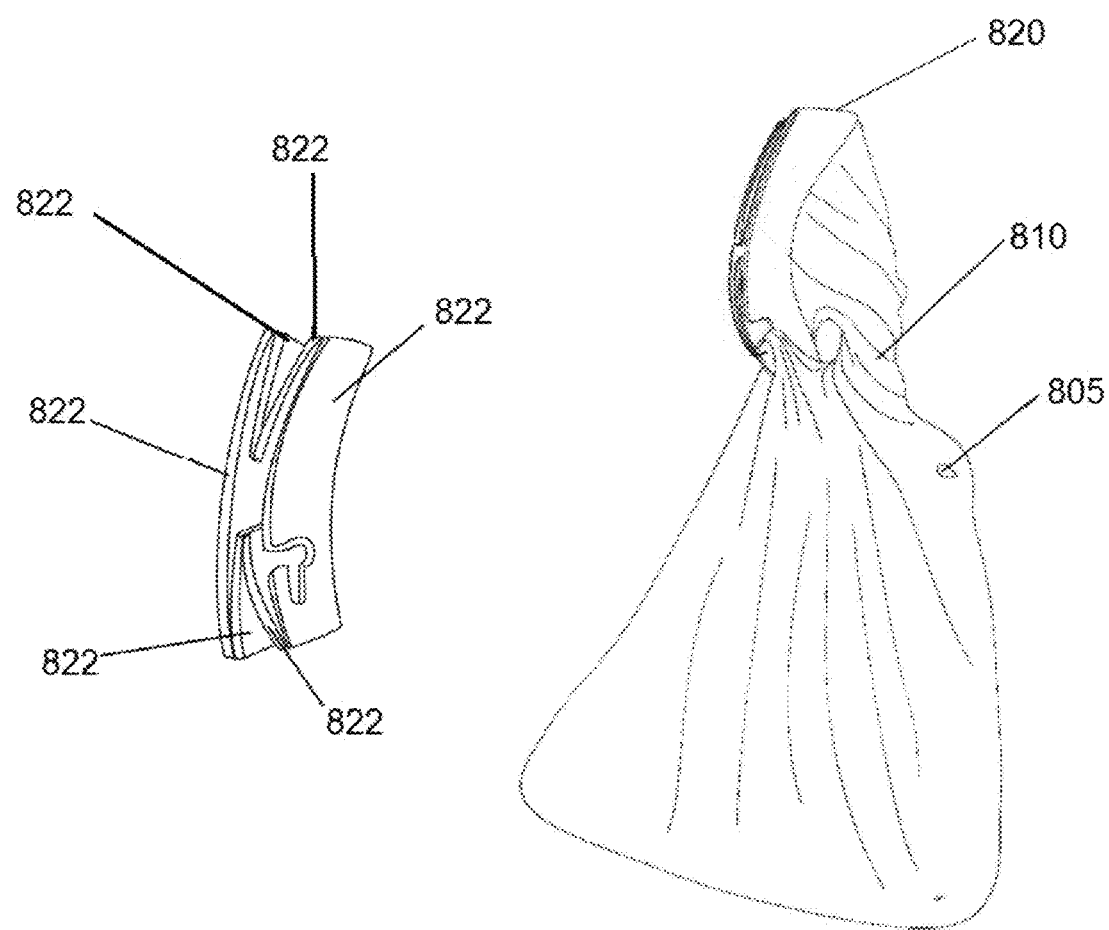
FIG. 27 is a perspective view of a disposable bag having a foldable collar being collapsed and engaged with an aperture on the shoulder of the bag.

As mentioned earlier, the bag roller 410 can have various types of receiving and/or protruding structures as an attachment mechanism to couple to a collar of a bag 500. FIG. 17 shows another rotatable bag roller 310 having a protruding peg 345 for a user to hold to rotate the bag roller, and to pull upwards to unlock it from a position. The bag roller 310 can have a circular short wall 346 and three short cylindrical stubs 347. In FIG. 18, a particular embodiment of disposable bag has a flat, planar, and foldable collar 820 with three through-holes 881 to receive the three short cylindrical stubs 347 on the bag roller 310. The flat planar collar 820 has 6 pre-scored folding lines, allowing the collar to collapse upon itself as shown in FIG. 27. In FIG. 27, the collar has six collar panels 822 that are consecutively and pivotably connected one to another. When they collapse, four of the collar panels 822 are sandwiched by two of the collar panels 822. Any number of collar panels 822 are contemplated and are specifically disclosed in co-pending patent application referenced to above, which is herein incorporated by reference in its entirety.

Figure 19:
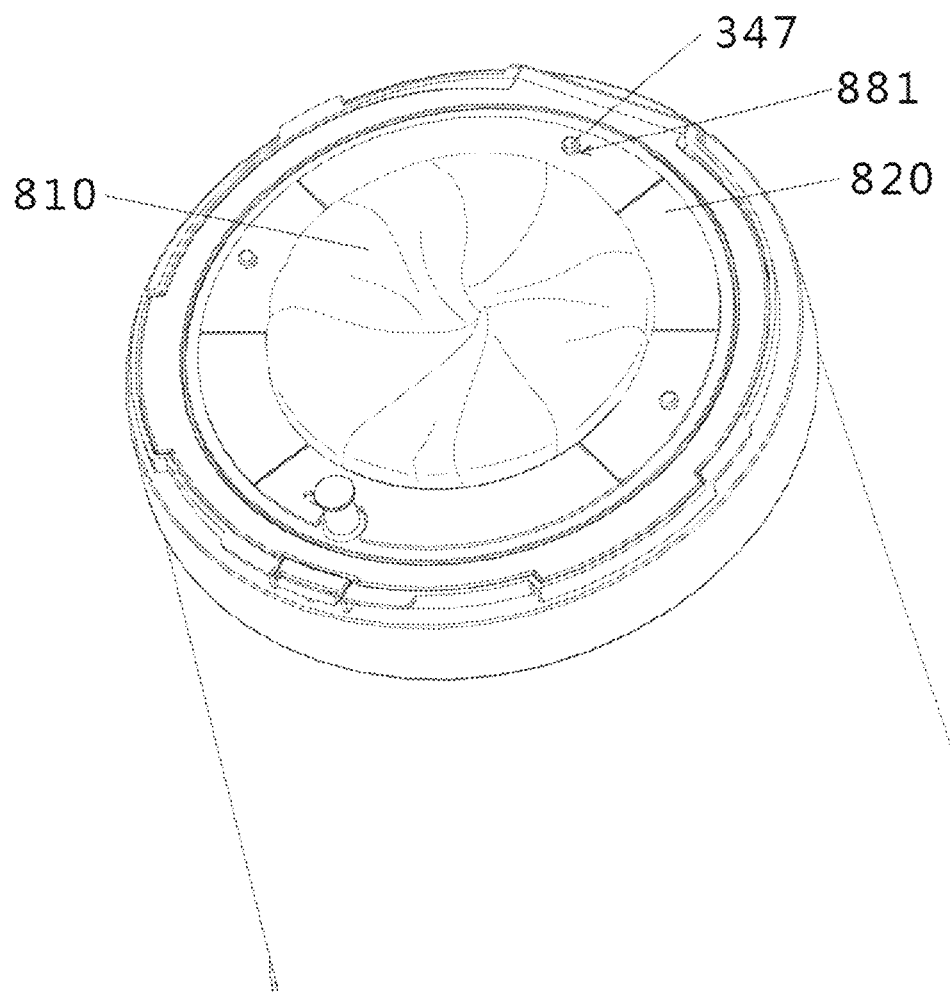
FIG. 19 shows another disposable bag having a foldable collar installed onto the frame assembly of FIG. 17 using couplers.

FIG. 19 shows the collar 820 installed on the bag roller 310 and the three short cylindrical stubs 347 fully inserted through the three through-holes 881. Furthermore, FIG. 19 shows a twisted neck 810 caused by having rotated the bag roller 310 from a first position to a second position, after the collar 820 was installed.

Although the bag roller 310 is shown to have short cylindrical stubs 347 as its bag/collar attachment mechanism, contemplated attachment mechanisms can have any shapes and structures capable of making coupling contact, mating contact, frictional contact, or abutting contact with a contemplated collar of corresponding shapes. For example, the bag roller 310 can have narrow slits where a part of a flat planar collar can fold and insert into, thereby locking itself in place. The bag roller 310 can also have other receiving structures such as a raised platform with a lateral groove for a flat planar collar to slide into or snap into.

Figure 20A:
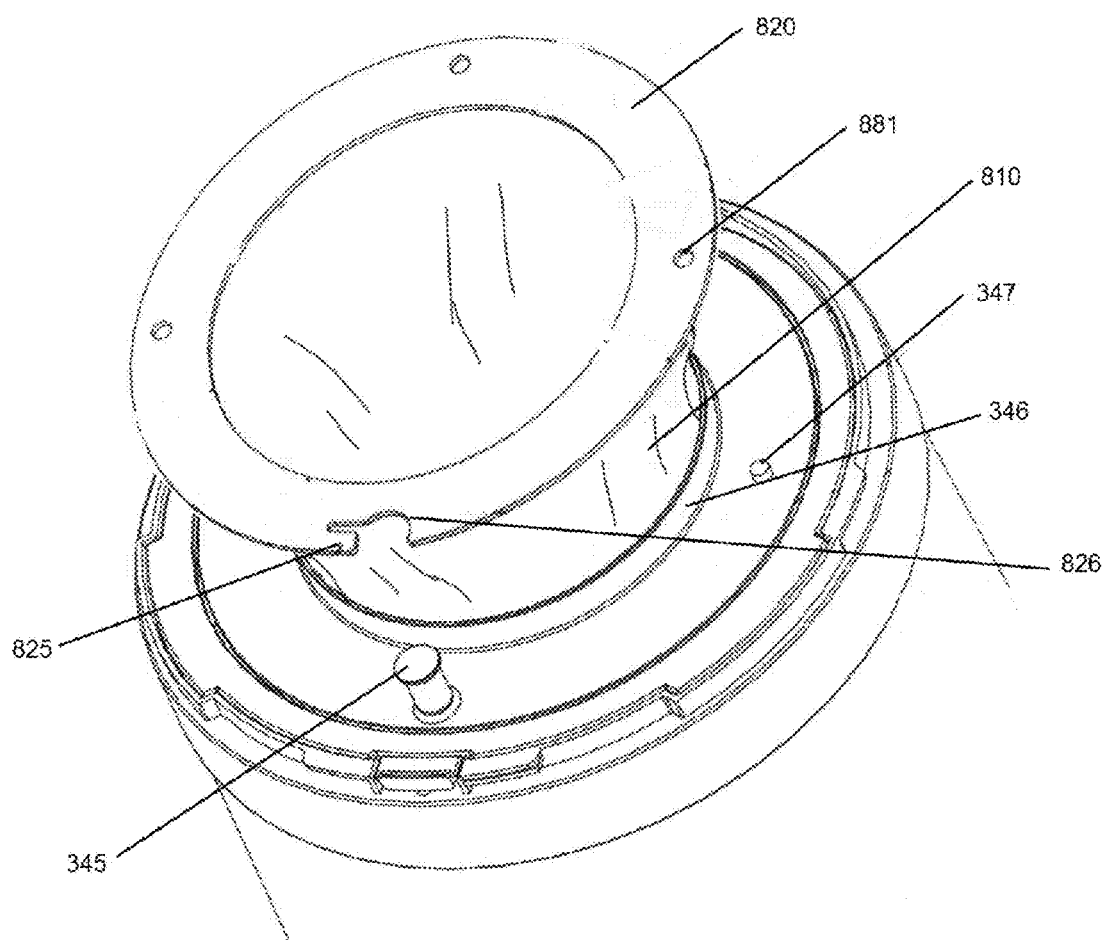
FIG. 20A shows a disposable bag having a non-foldable collar being installed onto the frame assembly of FIG. 17.
Figure 20B:
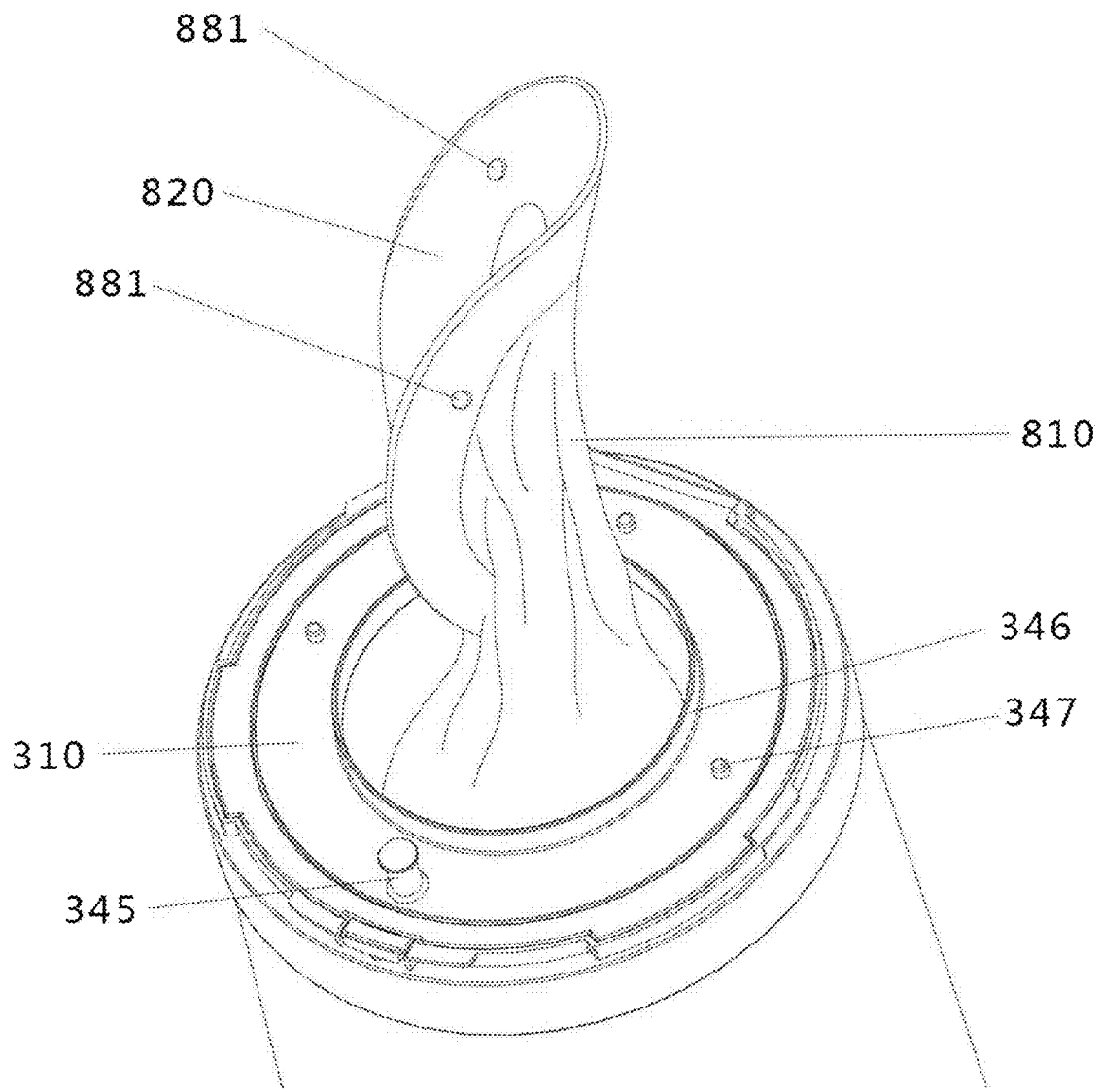
FIG. 20B shows a disposable bag having a non-foldable collar being deformed in order to pass the bag collar through the frame assembly.

FIGS. 20A and 20B show one embodiment where the collar 820 do not have pre-scored folding lines and where the collar 820 is flexible and can be deformed (without having to collapse or fold upon itself) before passing through the opening defined by short circular wall 346. The collar 820 is shown to have a locking notch 826 and a finger 825 for receiving the twisted neck 810 therein when removing the bag from the diaper pail. In another embodiment, the locking notch 826 and the finger 825 are configured to engage with bag attachment mechanisms 505, 805 when removing the bag from the diaper pail.

Figure 21:
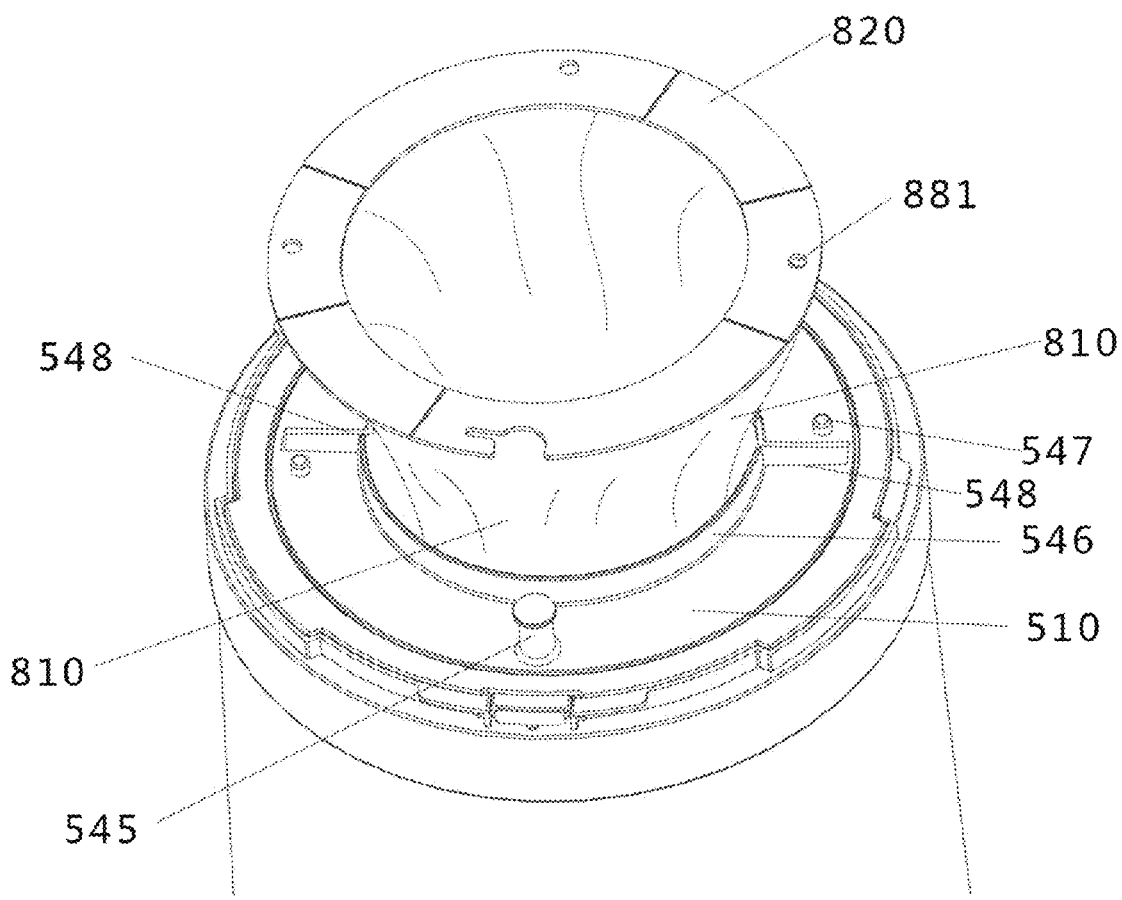
FIG. 21 shows a frame assembly having a slot opening which allows the bag collar to pass through without having to fold or deform the bag collar.

FIG. 21 shows another embodiment where the collar 820 can pass through the opening defined by short circular wall 446 without deforming/collapsing/folding the collar 820 because the contemplated bag roller 510 has a slot 548. The slot 548 is configured as an elongated opening sufficiently wide to receive the collar 820 therethrough.

Additionally, a waste receptacle does not typically serve as a decorative or visually stimulating article in the room. In other words, the waste receptacle is typically not an article of interest or stimulation for infants and toddlers. A visually stimulating diaper pail could serve to reinforce infant-toddler behavior and to enable infants and toddlers to alert parents to time for a diaper change since the child would be excited to view the visually stimulating event that accompanies diaper disposal. It can be further appreciated that a desirable waste disposal system also further serves as a visually stimulating system that can reinforce positive infant-toddler behavior, afford child/parent bonding experience and assist in child development.

It is known that vision may be one of the least developed senses at birth, therefore visual input during the early months may have the most profound effect on a baby's development of the nervous system. While an adult can distinguish many different shades of light and color, a newborn retina can only detect large contrasts between dark and light, or black and white. As the baby grows, the brain receives input from all five senses, causing nerve cells to multiply and form connections with other nerve cells. Studies have suggested that if a baby is kept blindfolded the visual center in his/her brain would never develop. One of the best ways to stimulate a baby's vision is to use contrasting colors and stripes. As described above, the outer barrel casing 200 can be transparent, allowing a user and the baby to see vibrant, rotating colorful designs disposed on the inner barrel 210. This powerful visual stimulant can occur together with a diaper changing event. Up until now, for infants and toddlers, diaper changing has always been associated with negative feelings. Over time, the visually enticing diaper pail not only stimulates a baby's visual center in his/her brain, it also changes infant behavior by associating diaper changing with such visually fascinating spectacle acting as a positive reinforcement.

In the case of toddlers, they are old enough to be able to look down through the top transparent doors 110 of the diaper pail 10 and to see the soiled diaper being swallowed up by the untwisting of the bag 500. This also acts as a positive reinforcement in infant and toddler behavior development.

While the inner barrel 210 is shown in FIGS. 7A and 7B as having a spiral pattern or a spiral structure, also contemplated are visually enticing graphics, geometric shapes, and lines of contrasting colors, designs, photographs, solid colors, as well as depicting cartoon characters for visual attractiveness and stimulation.

Thus, specific embodiments and applications of system and apparatus for waste disposal and changing infant-toddler behavior have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Insubstantial changes from the claimed subject matter as viewed by a person with ordinary skill in the art, now known or later devised, are expressly contemplated as being equivalent within the scope of the claims. Therefore, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the disclosure. In addition, where the specification and claims refer to at least one of something selected from the group consisting of A, B, C . . . and N, the text should be interpreted as requiring only one element from the group, not A plus N, or B plus N, etc.

The words used in this specification to describe the disclosure and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims therefore include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

What is claimed is:

1. A diaper disposal system for holding a plurality of soiled diapers;
the system comprising:
a base;
an outer casing;
an inner barrel having an inner volume, and the inner barrel is rotatably disposed inside of the outer casing; and
a top chamber having at least one door disposed at a top of the top chamber;
an actuator to control a rotational movement of the inner barrel;
a first bag attachment mechanism coupled to the outer casing configured to detachably couple to a top rim of the disposable bag, and to keep the top rim stationary when a body portion of the disposable bag rotates along with the inner barrel;

a second bag attachment mechanism to detachably couple the body portion of the disposable bag to the inner barrel so the body portion rotates when the inner barrel rotates; and wherein the at least one door of the top chamber is transparent/translucent.

2. The diaper disposal system of claim 1, further comprising a clearance height between an upper rim of the disposable bag and the at least one door of the top chamber, wherein the clearance height is configured to be sufficiently tall to contain a soiled diaper between the twisted-closed neck and the at least one door of the top chamber, while the at least one door is closed.

3. The diaper disposal system of claim 2, wherein the at least one door of the top chamber is disposed horizontally at rest, perpendicular to a longitudinal axis of the inner barrel.

4. The diaper disposal system of claim 2, wherein the actuator comprises at least one of a foot pedal, a button, and a sensor; wherein when the actuator is at rest, a neck of the disposable bag is in a twisted-closed formation; wherein when the actuator is activated, the inner barrel rotates in a first direction untwisting the neck to an open formation; wherein when the actuator is deactivated, the inner barrel rotates in a second direction returning the neck to the twisted-closed formation.

5. The diaper disposal system of claim 4, wherein a movement of the at least one door of the top chamber is independent of the rotation of the inner barrel.

6. The diaper disposal system of claim 1, wherein the first bag attachment mechanism is a frame assembly disposed above the inner barrel, wherein the frame assembly comprises a roller base and a bag roller; and wherein the bag roller is rotatable relative to the roller base and is configured to be locked into a first position and a second position.

7. The diaper disposal system of claim 6, wherein the first bag attachment mechanism has a protruding structure and/or a receiving structure configured to couple to a collar of the disposable bag.

8. The diaper disposal system of claim 6, wherein the frame assembly has a slot disposed through the roller base and the bag roller for the collar of the disposable bag to pass therethrough.

9. A waste disposal system comprising:
an outer casing;
a top chamber configured to hold a soiled diaper;
a top door leading into the top chamber;
an enclosure area disposed below the top chamber configured to receive the soiled diaper when it drops from the top chamber;
an entrance to the enclosure area disposed between the top chamber and the enclosure area;
an actuator to control an opening and a closing of the entrance to the enclosure area, and the opening of the entrance causes the soiled diaper to drop from the top chamber into the enclosure area; and
a frame assembly pivotably or removably coupled to the outer casing and disposed above the inner barrel, wherein the frame assembly comprises a roller base and a bag roller; wherein the bag roller is rotatable both clock-wise and counter clock-wise relative to the roller base, and wherein the first bag attachment mechanism is disposed on the bag roller.

10. The waste disposal system of claim 9, wherein the enclosure is a disposable bag, and wherein the closing of the entrance is created by twisting a neck portion of the disposable bag.

11. The waste disposal system of claim 10, further comprising an inner barrel rotatable relative to the outer casing, and wherein said first bag attachment mechanism is configured to detachably couple to a top rim of the disposable bag using a coupler, and the coupler keeps the top rim stationary when a body portion of the disposable bag rotates along with the inner barrel.

12. The waste disposal system of claim 10, wherein at least one of the top door and the outer casing is transparent.

13. The waste disposal system of claim 10, wherein the frame assembly has a slot allowing a collar of the disposable bag to pass therethrough.

14. A method of inspecting a fullness of a diaper container while minimizing escape of odor from the diaper container, the method comprising:
providing a container assembly having a top transparent door and an outer casing;
wherein the container assembly holds a disposable bag;
providing an actuator for a user to selectively control opening and closing of the disposable bag independent of the top transparent door being open or shut, thereby allowing visual inspection down into the disposable bag when the user selectively opens the bag while keeping the top transparent door closed.

15. The method of claim 14, further providing a clearance space between a top rim of the disposable bag and the top transparent door while the door is shut; wherein the clearance space is sufficiently tall to fit a soiled diaper.

16. The method of claim 14, wherein the actuator is controlled by a foot pedal.

* * * * *